(12) United States Patent
Obata

(10) Patent No.: US 8,980,180 B2
(45) Date of Patent: Mar. 17, 2015

(54) GEL PARTICLE MEASUREMENT DEVICE

(76) Inventor: Toru Obata, Tokyo (JP)

(*) Notice: Subject to any disclaimer, the term of this patent is extended or adjusted under 35 U.S.C. 154(b) by 0 days.

(21) Appl. No.: 13/701,773

(22) PCT Filed: May 23, 2011

(86) PCT No.: PCT/JP2011/061741
§ 371 (c)(1),
(2), (4) Date: Dec. 3, 2012

(87) PCT Pub. No.: WO2011/152236
PCT Pub. Date: Dec. 8, 2011

(65) Prior Publication Data
US 2013/0078150 A1 Mar. 28, 2013

(30) Foreign Application Priority Data
Jun. 4, 2010 (JP) .................................. 2010-129294

(51) Int. Cl.
*G01N 21/00* (2006.01)
*G01N 21/75* (2006.01)
(Continued)

(52) U.S. Cl.
CPC ................ *G01N 21/75* (2013.01); *G01N 15/06* (2013.01); *G01N 21/51* (2013.01); *G01N 21/82* (2013.01); *G01N 2015/003* (2013.01); *G01N 2021/4709* (2013.01); *G01N 2015/0693* (2013.01)
USPC .................................... 422/82.05; 422/82.09

(58) Field of Classification Search
USPC ............. 422/82.05, 82.09; 356/342, 335, 336
See application file for complete search history.

(56) References Cited

U.S. PATENT DOCUMENTS 5,907,399 A 5/1999 Shirasawa et al.
2005/0019842 A1* 1/2005 Prober et al. .................... 435/7.9

(Continued)

FOREIGN PATENT DOCUMENTS

EP 2081024 A1 7/2009
JP 2-23825 B2 5/1990
(Continued)

OTHER PUBLICATIONS

Castillo et al., "The effect of temperature and inoculum concentration an rheological and light scatter properties of milk coagulated by a combination of bacterial fermentation and chymosin. Cottage cheese-type gels". Int. Dairy J., Feb. 2006, vol. 16, No, 2, pp. 131-146.

(Continued)

*Primary Examiner* — Natalia Levkovich
(74) *Attorney, Agent, or Firm* — Birch, Stewart, Kolasch & Birch, LLP

(57) ABSTRACT

To measure a starting point of production of gel particles with high sensitivity in measurement of a target substance in a sample through a gelation reaction while minimizing light attenuation in a solvent in which a phenomenon occurs, provided is a gel particle measurement device including: a sample cuvet (1) accommodating a sample (S) and a solution containing a reagent (R); stirring means (2) for stirring a mixed solution (W); an incident light source (3) for irradiating the mixed solution (W) with coherent light (Bm); backscattered light detecting means (4) provided outside the sample cuvet (1) on the same side on which the incident light source (3) is provided, the backscattered light detecting means (4) detecting a backscattered light component, which returns toward the incident light source, in the light scattered in the mixed solution (W) in the sample cuvet (1); scattered light fluctuation measuring means (5) for measuring a fluctuation component of backscattered light based on a detection output from the backscattered light detecting means (4); and gel particle production determining means (6) for determining, based on a result of measurement by the scattered light fluctuation measuring means (5), a production state of gel particles, which includes at least a starting point of production of the gel particles, which leads to timing of phase transition of the mixed solution (W) from a sol phase to a gel phase.

11 Claims, 17 Drawing Sheets

(51) Int. Cl.
*G01N 15/06* (2006.01)
*G01N 21/51* (2006.01)
*G01N 21/82* (2006.01)
G01N 15/00 (2006.01)
G01N 21/47 (2006.01)

(56) References Cited

U.S. PATENT DOCUMENTS

2005/0225752 A1 10/2005 Takai et al.
2011/0013185 A1 1/2011 Obata

FOREIGN PATENT DOCUMENTS

| JP | 3-11423 B2 | 2/1991 |
| JP | 4-21821 B2 | 4/1992 |
| JP | 5-215666 A | 8/1993 |
| JP | 3199850 B2 | 8/2001 |
| JP | 2004-93536 A | 3/2004 |
| JP | 2008-191170 A | 8/2008 |
| WO | WO 2008/038329 A1 | 4/2008 |
| WO | WO 2009/116633 A1 | 9/2009 |
| WO | WO 2010/038628 A1 | 4/2010 |

OTHER PUBLICATIONS

International Search Report mailed on August 16, 2011, issued in PCT/JP2011/061741.
Wang et al., "Predicting cottage cheese cutting time using a light backscatter sensor", Milchwisserischaft, 2005, vol. 60, No. 2, pp. 164-167.

* cited by examiner

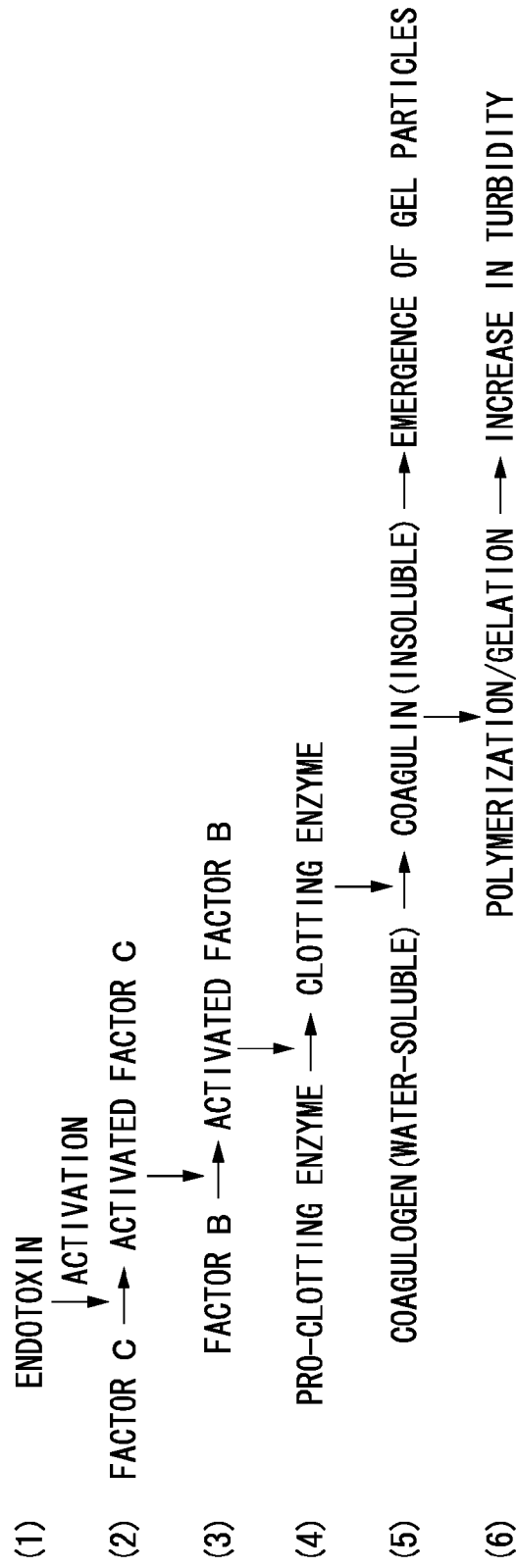

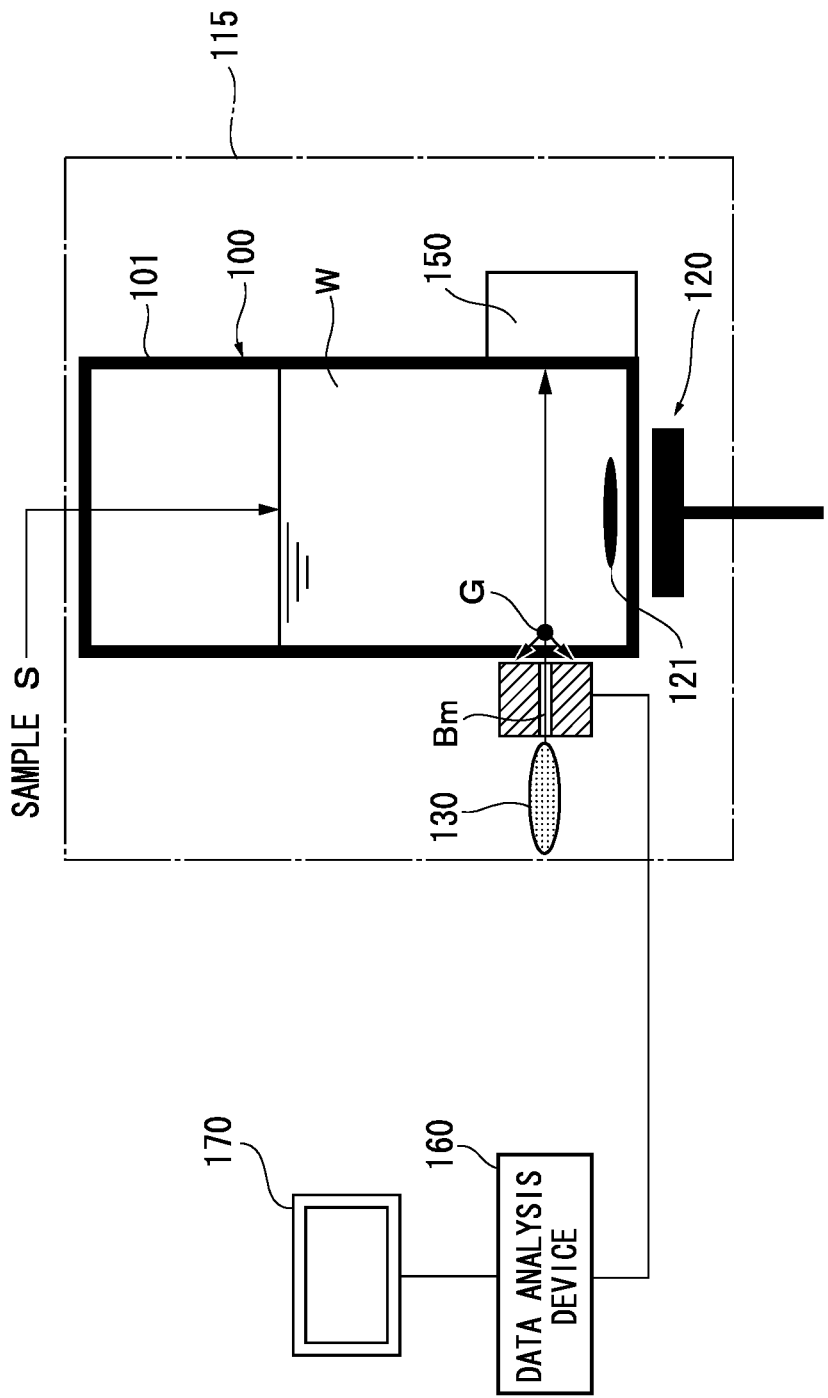

DETECTION EXAMPLE OF GEL PARTICLES
BY BACKSCATTERED MEASURING LIGHT

CALIBRATION CURVE

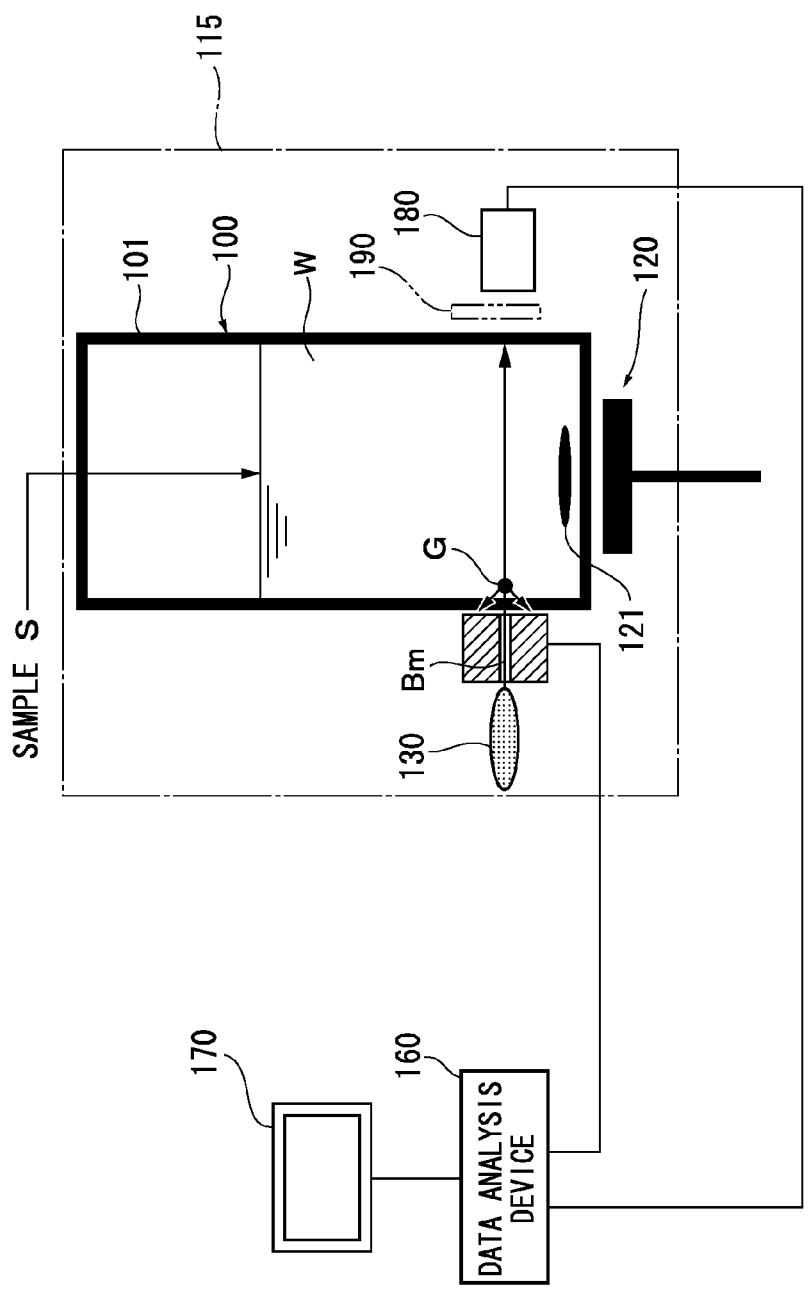

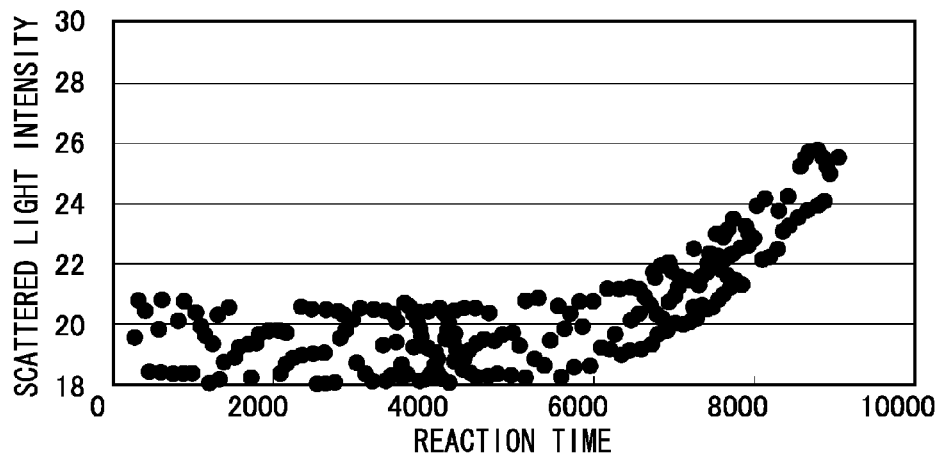
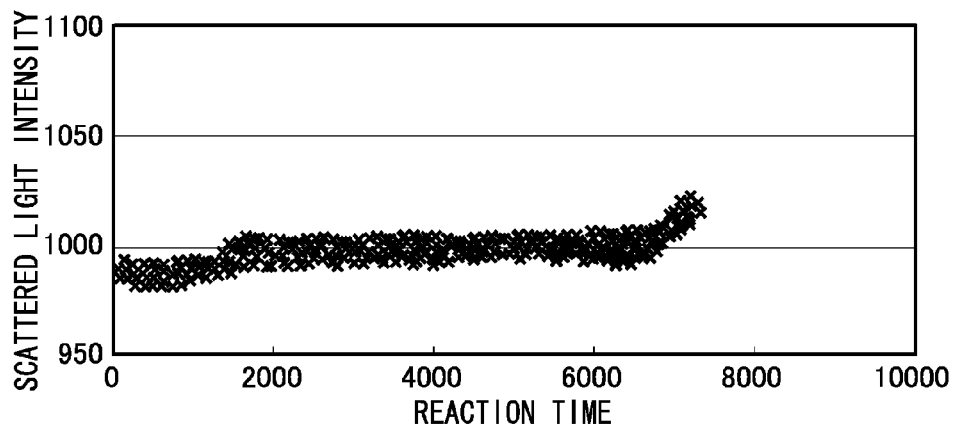
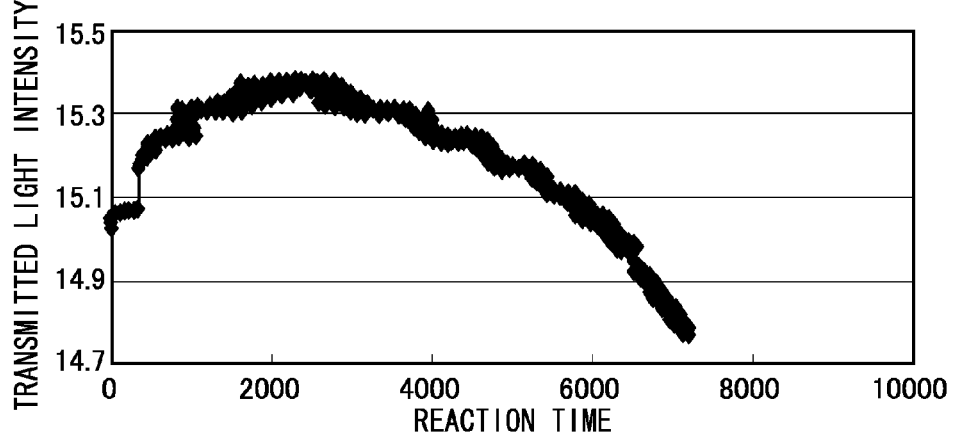

FORMATION OF PARTICLES

FORMATION OF PARTICLES

GEL PARTICLE MEASUREMENT DEVICE

TECHNICAL FIELD

The present invention relates to a gel particle measurement device for measuring particles produced from a target substance such as an endotoxin or a β-D-glucan in a sample as a measuring object by a gelation reaction, and in particular relates to the gel particle measuring device which can measure a starting point of production of gel particles with high sensitivity.

BACKGROUND ART

So-called endotoxins (intracellular toxins) mainly include fragments of cells of bacteria that are not stained by Gram staining (Gram-negative), and a component of the fragments is a lipid-polysaccharide called a lipopolysaccharide. To be specific, the component is a lipopolysaccharide (LPS) in which a lipid called Lipid A and a polysaccharide chain are bonded via 2-keto-3-deoxyoctonate (KDO). A lipid component called Lipid A included in the lipopolysaccharide is bonded to a cellular receptor, causing inflammation, and causing a variety of severe clinical symptoms in many cases. The endotoxins are, as described above, substances causing clinical symptoms such as sepsis and bacteremia that are high in fatality. Thus, estimation of the endotoxins present in the body is highly demanded clinically.

Further, it is important that medicinal products (such as injections) and medical devices (such as angiocatheters) are free of endotoxin contamination (pyrogen-free), and it is strictly required that endotoxins be completely removed from medicinal products (such as recombinant proteins and DNA used for gene therapies) prepared by using bacteria.

In confirmation of the removal of endotoxins or measurement of endotoxins in emergency medicine, promptness is required for attaining the purposes of copying with a large number of measuring samples and carrying out life-saving treatment.

Research has been made since old days on measuring the value of endotoxins for the treatment of sepsis or the like. Since the discovery of a fact that a factor group contained in the component of an amebocyte of a horseshoe crab (*Limulus polyphemus*) specifically reacts with endotoxins, resulting in gelation, trials for quantifying the endotoxins have been made by using limulus amebocyte lysates (LAL reagent or limulus reagent).

A measuring method in which the limulus reagent was used for the first time was a simple measuring method called a gelation method, in which plasma from a patient serving as a sample is mixed with the limulus reagent, the mixture is left to stand still, the mixture is positioned up side down after a certain time, the presence or absence of gelation is confirmed by whether or not the solution is solidified, and the amount of endotoxins is estimated based on the maximum dilution ratio at which the gelation is caused.

Later, attention has been paid to the increase of turbidity during a gelation reaction. As a result, there is known a turbidimetric assay, in which a turbidimeter using an optical measuring method is used to measure an endotoxin concentration based on changing speed in turbidity involved in the gelation reaction.

In addition, a synthetic chromogenic substrate method has already been known, in which method a gelation reaction causing a conversion from coagulogen to coagulin is replaced by a chromogenic reaction of a synthetic substrate in the final stage of a reaction process caused by a limulus reagent. This is a method in which a synthetic chromogenic substrate (Boc-Leu-Gly-Arg-p-nitroanilide) is added in place of a coagulation precursor (coagulogen) in a coagulation process, the hydrolysis of the synthetic chromogenic substrate then produces free p-nitroaniline, and the colorimetric analysis of the resultant yellow chromogenic development is performed to measure an endotoxin concentration.

Besides, the following measuring apparatuses disclosed in Patent Documents 1 and 2 are exemplified as a conventional gelation reaction measuring apparatus or a measuring apparatus associated with the conventional gelation reaction measuring apparatus.

Patent Document 1 does not relate to a gelation reaction measuring apparatus, but relates to a method of measuring the size and number of the aggregated clumps of platelets in blood at each of the processes in which the platelets aggregate and grow as clumps. This is a method in which a sample in a sample cuvet is irradiated with an illuminating radiation from a laser light source, the scattered light that has been scattered laterally by 90° because of the presence of the platelets is partially detected with a photodetector, and the size and number of the aggregated clumps of the platelets are measured based on the detection results.

Further, Patent Document 2 relates to a gelation reaction measuring apparatus using a turbidimetric assay. This is an assay in which the time-dependent changes of the intensity of transmitted light in a mixture obtained by mixing a specimen (sample) and a limulus reagent are measured, and an endotoxin concentration in the specimen is measured based on the amounts of the changes in a predetermined time.

Further, Patent Document 3 relates to a gelation reaction measuring apparatus for measuring the concentration of a target substance such as endotoxins in a sample via a gelation reaction. This includes a photoreceptive element for receiving a laser beam of light scattered by gel particles generated in a sample cuvet, and measuring means for measuring the diameter of the gel particles and the number thereof on time series based on the output of the scattered light detection of the photoreceptive element.

According to Patent Documents 1-3, when the sample in the sample cuvet is irradiated with the illuminating radiation from the laser light source, the scattered light which leaves for the side that is different from the side installed the laser light source; for example the front scattered light which leaves for the front side which is opposite the laser light source or the other side scattered light which leaves for the other side laterally by 90° from the laser light source is detected with the photodetector, and these gelation reaction measuring apparatus measure the aggregated clumps of the platelet which is measurement subject or the endotoxin concentration based on detected result of the photodetector.

Moreover, measuring techniques using a gelation reaction are used for measuring not only the endotoxins described above but also β-D-glucans or the like.

β-D-glucans are polysaccharides constituting cell membranes specific to fungi. Measurement of the β-D-glucans is effective for screening a wide variety of fungi responsible for fungal infection, including not only fungi found in a general clinical environment, such as *Candida, Aspergillus*, or *Cryptococcus*, but also fungi rarely found in the general clinical environment.

The phenomenon in which a component extracted from a amebocyte of a limulus is gelated with β-D-glucans is also used in the measurement of β-D-glucans, and the above-mentioned gelation method, turbidimetric assay, or synthetic chromogenic substrate method is used to carry out the measurement.

Measuring techniques of endotoxins and of β-D-glucans have common points. For example, almost the same kind of measuring hardware is used to remove a Factor G component from the components extracted from amebocyte of *Limulus*, and hence a gelation reaction or chromogenic reaction selective to endotoxins can be measured. Alternatively, endotoxins in a sample are inactivated by pretreatment, and hence a gelation reaction or chromogenic reaction selective to β-D-glucans can be measured.

Patent Document 1: JP 3199850 B2 (Examples and FIG. 1)
Patent Document 2: JP 2004-93536 A (Modes for carrying out the Invention and FIG. 3)
Patent Document 3: WO2008/038329 A (Best mode for carrying out the invention and FIG. 1)

DISCLOSURE OF THE INVENTION

Problems to be Solved by the Invention

However, the gelation method, turbidimetric assay, and synthetic chromogenic substrate method, all of which have been conventionally used, have the following drawbacks.

Both the gelation method and the turbidimetric assay need as long a time as about 90 minutes or longer under low concentrations for the production of gels to take place. That is, although the gelation time of a reaction solution is proportional to the concentration of a target substance in a sample as a measuring object, it is not possible to detect the accurate starting time of gelation or the like by both the gelation method and the turbidimetric assay because of inferior sensitivity, and hence a reaction amount is calculated based on the time until the completion of the gelation, and the reaction amount serves as an indication for the gelation time.

The turbidimetric assay is taken as an example. By using the turbidimetric assay, it is possible to identify the initial turbidity level at which a change starts and the level at which the change arrives, but it is hard to identify the time at which each change starts and the time at which the each change finishes. Thus, the turbidimetric assay has been estimated as a quantification method in which measurement of a change at a certain level (increase in turbidity) between the initial level and the final level is carried out instead of the observation of a change in whole gelation. However, when the concentration of endotoxins is low, the gelation of the whole system is delayed, and at the same time, a change in turbidity to be observed is expanded, resulting in a difficulty in measuring the change in turbidity. As a result, sensitivity inevitably declines.

Thus, it is hard to say that both the gelation method and the turbidimetric assay are suitable for the case where emergency is required and for the measurement of many specimens. Besides, when the turbidimetric assay is carried out, non-specific turbidity irrelevant to endotoxins occurs in some cases, and hence the turbidimetric assay may lack measurement accuracy. Moreover, the critical concentration for measurement in the gelation method is 3 pg/ml, and the critical concentration for measurement in the turbidimetric assay is about 1 pg/ml.

Note that even if the scattering photometry disclosed in Patent Document 1 is applied as a turbidimetric assay applied to a gelation-reaction measuring apparatus, the scattering photometry is a quantification method in which the observation of the change in whole gelation is not carried out, and hence the above-mentioned problems cannot be solved.

On the other hand, the measurement time of the synthetic chromogenic substrate method is as short as about 30 minutes compared with those of the gelation method and turbidimetric assay. However, because a non-specific reaction occurs in some cases, the synthetic chromogenic substrate method has a difficulty in carrying out measurement with accurate specificity. Besides, in the synthetic chromogenic substrate method, preparation for measurement is troublesome, and the critical concentration for measurement is 3 pg/ml, which is inferior to the turbidimetric assay.

The present invention provides a gel particle measurement device, which can measure a starting point of production of gel particles with high sensitivity under mixing condition including a sample and a solution containing a reagent while minimizing light attenuation in a solvent in which a phenomenon occurs, when a target substance in the sample is measured through a gelation reaction.

MEANS FOR SOLVING THE PROBLEMS

First aspect of the invention according to claim 1 is a gel particle measurement device for measuring particles produced from a target substance in a sample through a gelation reaction, the device including: a sample cuvet at least partially comprising an incident portion through which light enters, and accommodating a sample containing a target substance to be measured and a solution containing a reagent that causes gelation of the target substance; stirring means for stirring a mixed solution comprising the sample and the solution containing the reagent in the sample cuvet so as to inhibit gelation of the entire mixed solution; an incident light source provided outside the incident portion of the sample cuvet, for irradiating the mixed solution comprising the sample and the solution containing the reagent in the sample cuvet with coherent light; backscattered light detecting means provided outside the incident portion of the sample cuvet on the same side on which the incident light source is provided, the backscattered light detecting means detecting a backscattered light component, which returns toward the incident light source, in the light scattered in the mixed solution comprising the sample and the solution containing the reagent in the sample cuvet; scattered light fluctuation measuring means for measuring a fluctuation component of scattered light based on a detection output from the backscattered light detecting means; and gel particle production determining means for determining, based on a result of measurement by the scattered light fluctuation measuring means, a production state of gel particles, which includes at least a starting point of production of the gel particles in the mixed solution, which leads to timing of phase transition of the mixed solution from a sol phase to a gel phase.

Second aspect of the invention according to claim 2 is a gel particle measurement device according to claim 1, in which the incident light source comprises a laser light source.

Third aspect of the invention according to claim 3 is a gel particle measurement device according to claim 1, in which the sample cuvet comprises, in a cell container, stirring means capable of directly stirring the sample and the solution containing the reagent.

Fourth aspect of the invention according to claim 4 is a gel particle measurement device according to claim 1, in which the sample cuvet is provided in a thermostatic chamber.

Fifth aspect of the invention according to claim 5 is a gel particle measurement device according to claim 1, in which the sample cuvet comprises, in the sample cuvet or around the sample cuvet, stray light removing means for removing a stray light component, which is generated by transmission or scattering, except the backscattered light component, which returns toward the incident light source in the mixed solution, in irradiation light from the incident light source.

Sixth aspect of the invention according to claim 6 is a gel particle measurement device according to claim 1, further including display means for displaying a result of determination by the gel particle production determining means.

Seventh aspect of the invention according to claim 7 is a gel particle measurement device according to claim 1, in which the backscattered light detecting means comprises a ring-shaped detection surface surrounding incident light which enters the sample cuvet from the incident light source.

Eighth aspect of the invention according to claim 8 is a gel particle measurement device according to claim 1, in which the backscattered light detecting means comprises a light-guiding member made of a light-transmissive fiber bundle surrounding incident light which enters the sample cuvet from the incident light source, the light-guiding member having one end functioning as a light introduction surface, the backscattered light detecting means having a detection surface placed corresponding to another end of the light-guiding member.

Ninth aspect of the invention according to claim 9 is a gel particle measurement device according to claim 1, further including: first scattered light detecting means serving as the backscattered light detecting means for detecting the backscattered light component, which returns toward the incident light source, in the light scattered in the mixed solution; second scattered light detecting means for detecting a scattered light component except the backscattered light component, which returns toward the incident light source, in the light scattered in the mixed solution; and scattered light fluctuation measuring means for measuring a fluctuation component of each scattered light based on detection outputs from the first and the second scattered light detecting means, in which the gel particle production determining means is configured to: determine the starting point of production of the gel particles in the mixed solution based on a result of measurement of the fluctuation component in the detection output from the first scattered light detecting means; and determine production state information of the gel particles at points except the starting point of production of the gel particles in the mixed solution based on a result of measurement of the fluctuation component in the detection output from the first scattered light detecting means and the detection output from the second scattered light detecting means or based on a result of measurement of the fluctuation component in the detection output from the second scattered light detecting means.

Tenth aspect of the invention according to claim 10 is a gel particle measurement device according to claim 1, in which: the target substance to be measured comprises an endotoxin; and the reagent for gelating the endotoxin comprises a limulus reagent.

Advantageous Effects of Invention

According to first aspect of the invention as defined in claim 1, when measuring a target substance in a sample through a gelation reaction, based on a fluctuation component of backscattered light, which returns toward the incident light source, in the scattered light scattered under mixing condition including a sample and a solution containing a reagent, a starting point of production of gel particles, which leads to the timing of phase transition of the mixed solution from a sol phase to a gel phase, can be measured with high sensitivity while minimizing light attenuation in a solvent in which a phenomenon occurs.

According to second aspect of the invention as defined in claim 2, the incident light source can be provided easily.

According to third aspect of the invention as defined in claim 3, the sample and the solution containing the reagent can be stirred more surely, and hence the production condition of the gel particles can be satisfied.

According to fourth aspect of the invention as defined in claim 4, the gelation reaction can be stably progressed under a thermostatic environment.

According to fifth aspect of the invention as defined in claim 5, it is possible to effectively prevent such a situation that a stray light component, which is generated by transmission or scattering, except a backscattered light component is detected erroneously by the backscattered light detecting means.

According to sixth aspect of the invention as defined in claim 6, the result of determination by the gel particle production determining means can be visually observed.

According to seventh aspect of the invention as defined in claim 7, accuracy of detection of a backscattered component by the backscattered light detecting means can be further enhanced.

According to eighth aspect of the invention as defined in claim 8, the backscattered light component can be detected efficiently by the backscattered light detecting means with a simple configuration.

According to ninth aspect of the invention as defined in claim 9, compared with an aspect in which the second scattered light detecting means is not used, the fluctuation component of the scattered light except the backscattered light, as well as the fluctuation component of the backscattered light, can be measured. Therefore, in addition to the starting point of production of the gel particles in the mixed solution, other production state information of the gel particles can be determined accurately.

According to tenth aspect of the invention as defined in claim 10, the present invention can be applied to quantification of an endotoxin.

BRIEF DESCRIPTION OF DRAWINGS

FIG. 3 is an explanatory diagram schematically illustrating a process of the gelation reaction of an endotoxin when a limulus reagent is used.

FIG. 5 is an explanatory diagram illustrating a gel particle measurement device according to a first embodiment of the present invention.

FIG. 11 is an explanatory diagram illustrating a gel particle measurement device according to a second embodiment of the present invention.

FIG. 14A is an explanatory graph showing an example of actually measured data obtained by irradiating a clinical hemolyzed whole blood sample with backscattered measuring light through use of the gel particle measurement device according to Example 1. FIG. 14B is an explanatory graph showing an example of actually measured data obtained by irradiating a clinical hemolyzed whole blood sample, which is similar to that of FIG. 14A, with forward scattered measuring light together with backscattered measuring light through use of the gel particle measurement device according to Comparative Example 1. FIG. 14C is an explanatory graph showing an example of actually measured data obtained by irradiating a clinical hemolyzed whole blood sample, which is similar to that of FIG. 14A, with forward transmitted light together with backscattered measuring light through use of the gel particle measurement device according to Comparative Example 2.

DESCRIPTION OF EMBODIMENTS

Summary of Embodiments

Figure 1:
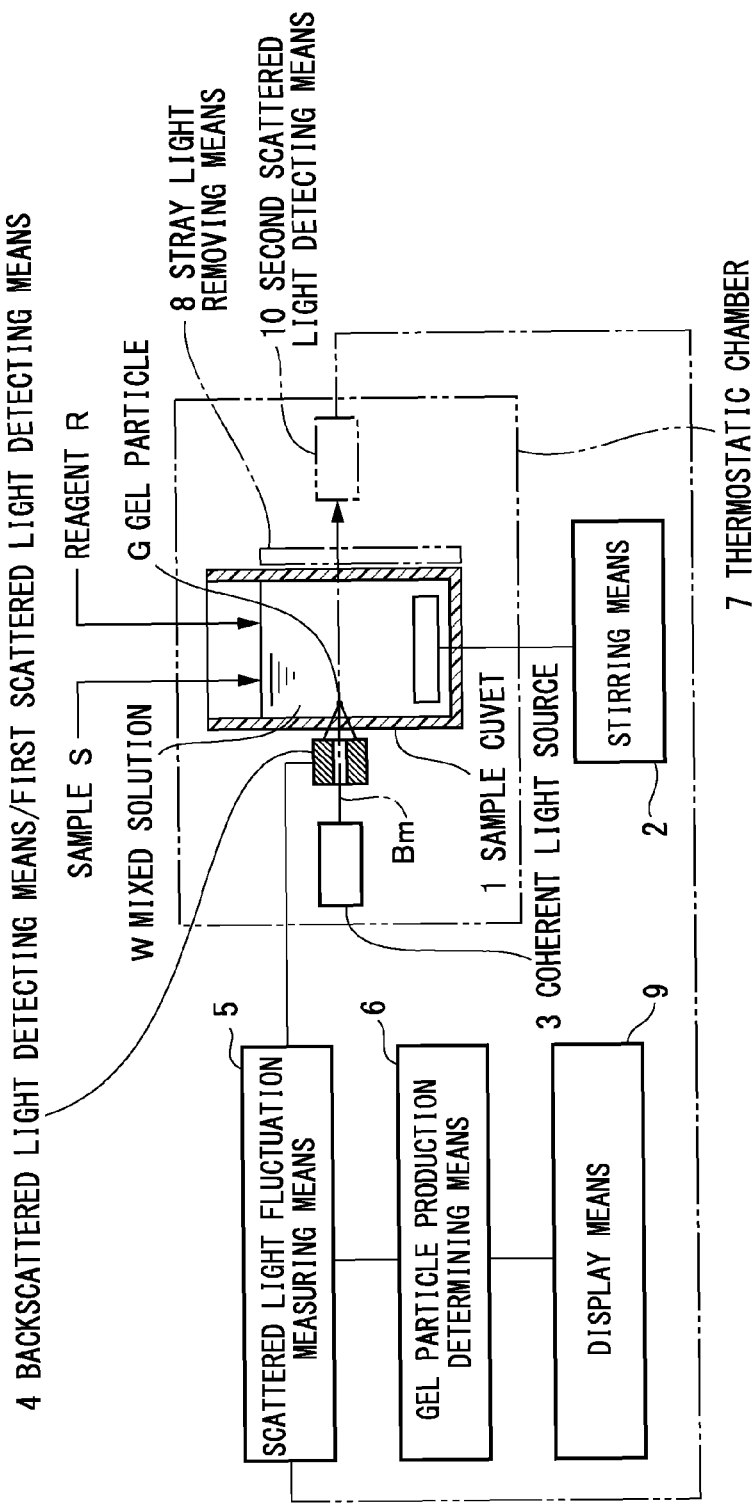
FIG. 1 is an explanatory diagram schematically illustrating a gel particle measurement device according to embodiments to which the present invention is applied.

FIG. 1 is an explanatory diagram schematically illustrating a gel particle measurement device according to embodiments to which the present invention is applied.

In FIG. 1, the gel particle measurement device is used for measuring particles produced from a target substance in a sample S through a gelation reaction. The gel particle measurement device includes: a sample cuvet 1 at least partially including an incident portion through which light enters, and accommodating the sample S containing the target substance to be measured and a solution containing a reagent R that causes gelation of the target substance; stirring means 2 for stirring a mixed solution W including the sample S and the solution containing the reagent R in the sample cuvet 1 so as to inhibit gelation of the entire mixed solution W; an incident light source 3 provided outside the incident portion of the sample cuvet 1, for irradiating the mixed solution W including the sample S and the solution containing the reagent R in the sample cuvet 1 with coherent light Bm; backscattered light detecting means 4 provided outside the incident portion of the sample cuvet 1 on the same side on which the incident light source 3 is provided, the backscattered light detecting means 4 detecting a backscattered light component, which returns toward the incident light source 3, in the light scattered in the mixed solution W including the sample S and the solution containing the reagent R in the sample cuvet 1; scattered light fluctuation measuring means 5 for measuring a fluctuation component of scattered light based on a detection output from the backscattered light detecting means 4; and gel particle production determining means 6 for determining, based on a result of measurement by the scattered light fluctuation measuring means 5, a production state of gel particles, which includes at least a starting point of production of gel particles G in the mixed solution W, which leads to timing of phase transition of the mixed solution W from a sol phase to a gel phase.

In such technical means, the target substance of the present invention widely includes any substance that is subjected to a gelation reaction with a predetermined reagent to produce gel particles. Examples of the target substance include an endotoxin and a β-D-glucan, and an example of the predetermined reagent in this case is a limulus reagent.

Further, the sample cuvet 1 is not limited to a shape having a cylindrical peripheral wall as long as the sample cuvet 1 at least partially includes an incident portion through which light enters, and may have a polygonal peripheral wall.

Note that, when light such as scattered light and transmitted light except backscattered light returning toward the backscattered light detecting means 4 in the light entering the incident portion is reflected from and scattered by an inner wall of the sample cuvet 1, there is a fear that part of the reflected and scattered light may be detected erroneously by the backscattered light detecting means 4 as stray light, and hence, it is preferred to employ a configuration in which such stray light influencing detection is not generated.

Further, from the viewpoint of keeping a measurement condition constant, a preferred mode is that the sample cuvet 1 is provided in a thermostatic chamber 7.

Besides, the stirring means 2 includes a wide range of means as long as the means provides a stirring action to the mixed solution W including the sample S and the solution containing the reagent R. A mode in which means is built in and directly performs stirring may be included of course, and any mode may be suitably selected from, for example, a mode in which a stirring action is provided by air and a mode in which a stirring action is provided by shaking.

Here, the degree of stirring by the stirring means 2 is required to be such that the entire mixed solution W including the sample S and the solution containing the reagent R in the sample cuvet 1 is inhibited from gelation.

In particular, from the viewpoint that stirring movement by the stirring means 2 may be conducted for sure, it is preferred that the sample cuvet 1 include, in a cell container, the stirring means 2 which is capable of directly stirring the mixed solution W including the sample S and the solution containing the reagent R.

Still further, the incident light source 3 is not limited to the laser light source for emitting laser light as long as coherent light is emitted. For example, the incident light source 3 may also be constructed by passing monochromatic light such as light of a sodium lamp through a pin hole, and may have a configuration using a high-brightness LED and a filter.

Further, the backscattered light detecting means 4 only needs to detect a backscattered light component, which returns toward the incident light source 3, in the light Bm entering the sample cuvet 1 from the incident light source 3 and scattered in the sample S and the solution containing the reagent R. In this case, the backscattered light detecting means 4 may directly detect the backscattered light component around the incident light from the incident light source 3, or may detect light by collecting light around the incident light from the incident light source 3 and guiding the light to an arbitrary place by a light-guiding member such as a glass fiber. Further, it is preferred to employ stray light removing means 8 for removing a stray light component (having a structure in which a light absorbing member is provided inside or outside the peripheral wall of the sample cuvet 1 or light is randomly reflected from a sample) so that a transmitted or scattered light component that does not return toward the incident light source 3 in the mixed solution W in the light entering from the incident light source 3 is not detected as stray light by the backscattered light detecting means 4.

Besides, the scattered light fluctuation measuring means 5 only needs to measure the fluctuation component of scattered light based on the detection output from the backscattered light detecting means 4. Example of the scattered light fluctuation measuring means includes a technique that applies filtering to the detection output while applying averaging or smoothing thereto.

Still further, the gel particle production determining means 6 includes a wide range of means which determines the production state of the gel particles, which includes at least a starting point of production of the gel particles in the mixed solution W, which leads to the timing of phase transition of the mixed solution W from a sol phase to a gel phase.

In addition, the phrase "determine the production state of gel particles" of course includes direct determination of information regarding the production state of gel particles, and also includes determination of information that can be determined based on the production state of the gel particles (for example, quantified information on a target substance).

Here, the phrase "the production state of gel particles" widely includes the time point of the production start (emergence) of the gel particles, a change in the production process of the gel particles, the time point of the production finish of the gel particles, and the production amount of the gel particles. Thus, the phrase may herein include other matters, as long as the phrase includes at least the timing of phase transition of the mixed solution W from a sol phase to a gel phase.

Still further, from the viewpoint of visually observing the result of measurement by the scattered light fluctuation measuring means 5, it is preferred that there be provided display means 9 for displaying the result of measurement by the scattered light fluctuation measuring means 5.

Further, in this embodiment, the gel particle measurement device may include the above-mentioned backscattered light detecting means 4 as first scattered light detecting means, second scattered light detecting means 10 for detecting a scattered light component except the backscattered light component, which returns toward the incident light source 3, in the light scattered in the mixed solution W, and scattered light fluctuation measuring means 5 for measuring fluctuation components of the respective scattered light components based on detection outputs of the first and the second scattered light detecting means 4 and 10. The gel particle production determining means 6 may determine the starting point of the production of the gel particles G in the mixed solution based on a result of measurement of the fluctuation component in the detection output from the first scattered light detecting means 4, and determine production state information of the gel particles G at points except the starting point of the production of the gel particles G in the mixed solution W based on a result of measurement of the fluctuation component in the detection output from the first scattered light detecting means 4 and the detection output from the second scattered light detecting means 10 or based on a result of measurement of the fluctuation component in the detection output from the second scattered light detecting means 10.

Next, operation of the gel particle measurement device illustrated in FIG. 1 is described.

Figure 2A:
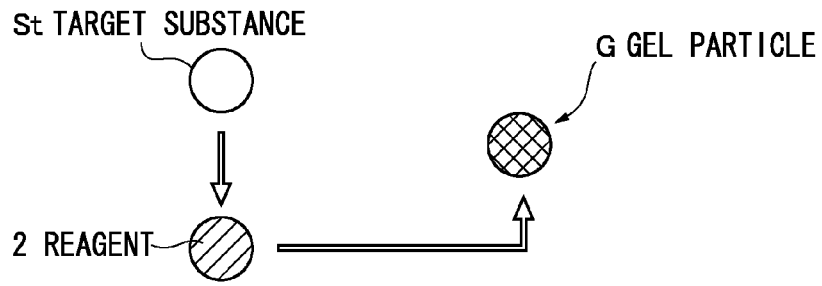
FIG. 2A is an explanatory diagram schematically illustrating a gelation reaction.

First, a gelation reaction is schematically illustrated in FIG. 2A.

In FIG. 2A, when a reagent R specifically reacting with a target substance St in a sample S is present, a phenomenon in which the target substance St specifically reacts with the reagent R takes place at a rate depending on the concentration of the target substance St in the sample S. In the process of the reaction, a given factor in the reagent R is activated by the stimulation of the target substance St, resulting in the activation of a given enzyme. Upon the activation, for example, a water-soluble protein may be converted to an insoluble protein through a decomposition reaction caused by the enzyme, resulting in emergence of a gel particle G.

More specifically, by taking an endotoxin as an example, a process of the gelation reaction of the endotoxin is schematically illustrated in FIG. 3.

In FIG. 3, after the stimulation of the endotoxin shown in (1) is delivered to a limulus reagent, Factor C is first activated into Activated Factor C by endotoxin as shown in (2). Next, the action of Activated Factor C causes the activation of Factor B, producing Activated Factor B as shown in (3). After that, the action of Activated Factor B causes the conversion of a pro-clotting enzyme to a clotting enzyme as shown in (4). As shown in (5), this clotting enzyme decomposes coagulogen (water-soluble protein), producing coagulin (insoluble protein). When stirring is performed under this condition, gelation of the entire coagulin (insoluble protein) is inhibited, and therefore a gel particle G of coagulin emerges. On the other hand, when the coagulin is left to stand still, polymerization and gelation take place to the entire solution system as shown in (6).

That is, in the case where the target substance St in the sample S is an endotoxin, when the stimulation of the endotoxin is delivered to the limulus reagent R while providing a constant stirring state to a mixed solution W to inhibit the gelation of the entire mixed solution W, the limulus reagent R can cause the production of the gel particles G of coagulin (insoluble protein) around the clotting enzyme. Thus, it is understood that after a gel particle G of coagulin (insoluble protein) is produced, a reaction process in which the gel particles G are subsequently produced follows.

Further, it was found that a rate at which the stimulation of the endotoxin was delivered to a flow of a reaction of the limulus reagent R (cascade) (limulus reaction rate) was dependent on an endotoxin concentration, and that as the endotoxin concentration was higher, the limulus reaction rate was higher, and the emerging timing of the gel particles G made of coagulin (insoluble protein) was earlier.

Thus, if changes in scattered light are detected with high accuracy, the emerging timing of the gel particles G made of coagulin (insoluble protein) can be observed as the starting point of the production of the gel particles G. This is a fundamental of the measuring principle of the gel particle measurement device according to this embodiment.

The measuring principle of the gel particle measurement device described above is completely different from, for example, the measuring principle of the conventional gelation method or conventional turbidimetric assay (the mode in which in the reaction process by the limulus reagent R under a static condition, gelation finally occurs owing to the influence of an activated clotting enzyme, and the gelated state is quantitatively measured based on the turbidity).

Figure 2B:
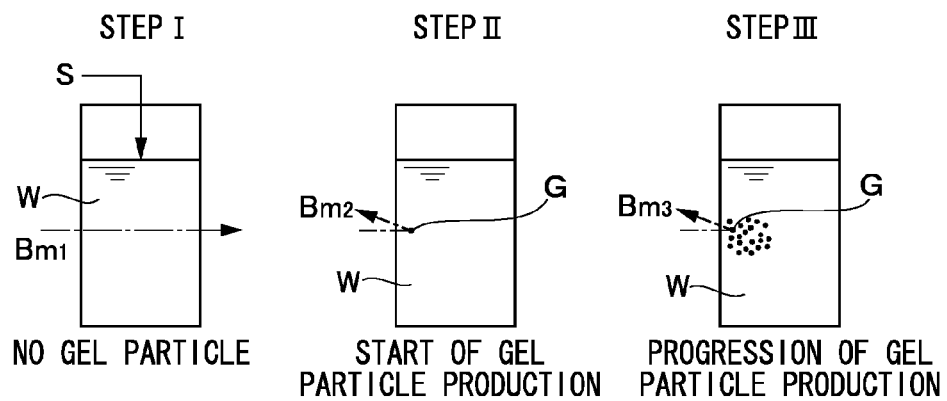
FIG. 2B is an explanatory diagram illustrating progressing steps I to III of the gelation reaction.

Here, the measuring principle of the gel particle measurement device is schematically illustrated in FIG. 2B.

Figure 2C:
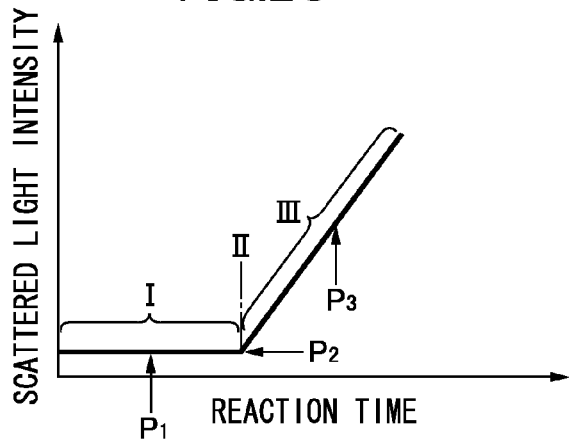
FIG. 2C is an explanatory graph showing a relationship between a reaction time and a scattered light intensity during the progressing steps of the gelation reaction.

In the gel particle measurement device of this embodiment, as illustrated in Step I in FIG. 2B, when the mixed solution W including the sample S and the solution containing the reagent R has no gel particle (corresponding to the case where the mixed solution W is in a sol phase), irradiation light $Bm_1$ from an incident light source (not shown) is not blocked by the gel particles. Thus, the irradiation light $Bm_1$ is not scattered by the gel particles, and hence, as a matter of course, there is no backscattered light component returning backward on the incident light source 3 side. Therefore, the scattered light intensity detected by the backscattered light detecting means 4 is kept substantially zero (see "$P_1$" of Step I in FIG. 2C).

Further, as illustrated in Step II in FIG. 2B, when the production of the gel particles G starts in the mixed solution W including the sample S and the solution containing the reagent R (corresponding to the case where the phase transition of the mixed solution W from a sol phase to a gel phase starts), if the gel particles G of coagulin (insoluble protein) in the case of, for example, an endotoxin start to be produced, irradiation light $Bm_2$ from the incident light source (not shown) is partially blocked by the presence of the produced gel particles G made of coagulin (insoluble protein). As a result, the irradiation light $Bm_2$ is scattered, and a backscattered light component, which returns toward the incident light source, in the scattered light is detected by the backscattered light detecting means 4. Therefore, the detection output from the backscattered light detecting means 4 is to rise to change from a zero-level that is a stable region (see "$P_2$" of Step II in FIG. 2C). In this case, the backscattered light immediately after the sample cuvet 1 to which incident light enters is detected substantially without being attenuated by a solvent.

After that, as illustrated in Step III in FIG. 2B, when the production of the gel particles G gradually progresses in the mixed solution W including the sample S and the solution containing the reagent R, the scattering degree of irradiation light $Bm_3$ from the incident light source (not shown) increases gradually due to the presence of many gel particles G which are sequentially produced, and a backscattered light component, which returns backward on the incident light source side and is to be detected by the backscattered light detecting means 4, also increases gradually. Therefore, the detection output from the backscattered light detecting means 4 increases sequentially, and the scattered light intensity detected by the backscattered light detecting means 4 is to rise to change sequentially after the change point $P_2$ (see "$P_3$" of Step III in FIG. 2C). On the other hand, when the intensity increases to some degree, the intensities of forward scattered light and sideward scattered light also increase more than attenuation in a solvent so as to be detected. However, initial scattering is not detected due to attenuation, and delayed from the backscattered light detection immediately after the sample cuvet 1.

In the embodiment described above, there is described a mode of determining a starting point of the production of gel particles (corresponding to "$P_2$" of Step II in FIG. 2B), which leads to the timing of phase transition of the mixed solution W from a sol phase to a gel phase significantly quickly compared with scattering in other directions, based on a fluctuation component of backscattered light of the irradiation light Bm which is irradiated in the mixed solution W.

In general, in the first place, measurement of an endotoxin in a clinical sample is required to be performed easily and quickly, in particular, for the purpose of emergency medical care.

Problems of "insufficient measurement caused by poor sensitivity" and "inconvenience caused by long measurement time" in a conventional turbidimetric assay can be solved without fail by the above-mentioned measurement system.

That is, in principle, the gel particle measurement device according to this embodiment is configured as follow. That is, the mixed solution W including a sample and a limulus reagent is stirred homogeneously to produce minute gel particles locally, not in the entire mixed solution system, under the homogeneous reaction. The gel particles are irradiated with coherent uniform light such as laser light to cause scattering of light. The scattered light is detected so as to detect a phase transition point leading to phase transition from a sol phase to a gel phase, which is emergence of gel particles due to the addition of an endotoxin. A time that elapses before the phase transition point is measured. In this manner, the amount of an endotoxin in the limulus reagent can be estimated.

In summary, the gel particle measurement device according to this embodiment is configured without keeping track of a change (gelation) in entire mixed solution system, paying attention to the fact that the timing of phase transition (starting point of the production of gel particles) depends on an endotoxin at agitated condition. Thus, an endotoxin can be detected more quickly compared with the conventional turbidimetric assay.

In particular, in this embodiment, attention is paid to a backscattered light component in the scattered light, which returns backward on the incident light source, and the reason for this is as follows.

Figure 4A:
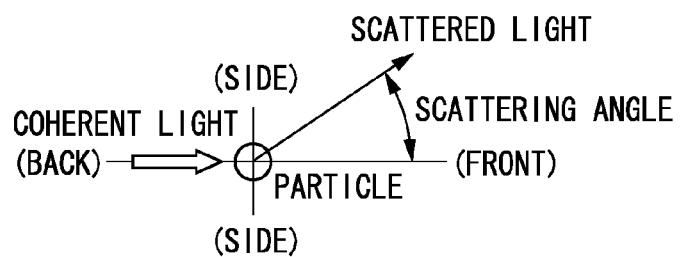
FIG. 4A is an explanatory diagram illustrating a scattering direction of scattered light when a gel particle is irradiated with coherent light.
Figure 4B:
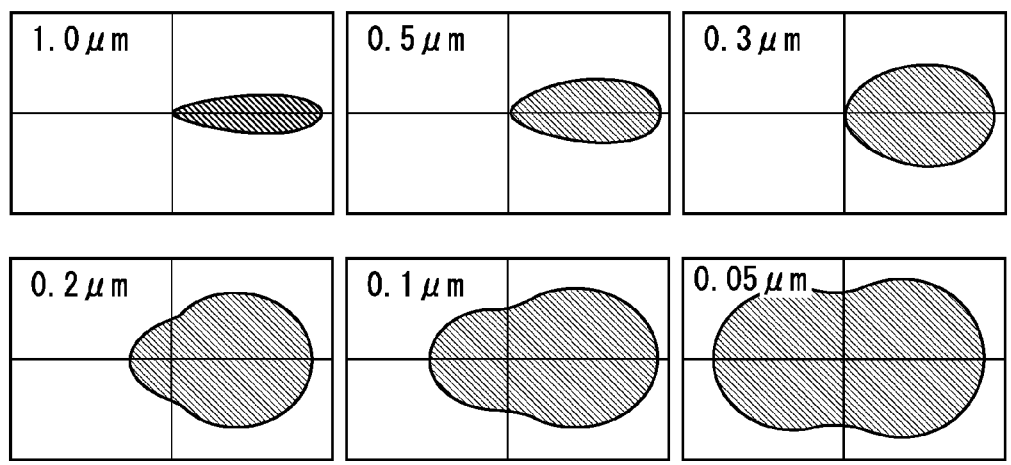
FIG. 4B is an explanatory diagram illustrating a luminosity distribution of scattered light involved in a change in particle diameter of the gel particle.

In general, as illustrated in FIG. 4A, assuming a model in which a particle is irradiated with coherent uniform light (coherent light) such as laser light, it is widely known that the coherent light is scattered due to the presence of the particle. A relationship between the size of the particle and the scattered light is examined in such a scattering phenomenon, and for example, a relationship as illustrated in FIG. 4B is observed in the intensity and directivity of the scattered light generated by the entrance of a single light beam. In FIG. 4B, the scattering phenomenon includes forward scattering that occurs in the same direction as that of light entering the particle, sideward scattering that occurs in a direction orthogonal to that of the light entering the particle, and backward scattering that occurs in a direction opposite to that of the light entering the particle.

In such a scattering phenomenon, considering a particle size and a scattering direction, apart from energy to be generated, forward scattering becomes more dominant as the particle size becomes larger, and scattering in all directions including backward scattering is observed when a particle size is small. According to such an observation result, forward scattering is considered to be advantageous in order to capture large particles. On the other hand, in order to quickly capture small particles produced first under a phenomenon in which particles come out of nothing and grow, any direction may be suitable. However, considering that energy is small, when attenuation of scattered light in a solvent in which particles are present is considered, backward scattering with less attenuation (less absorption caused by the influence of a solvent) is considered to be suitable.

Above all, it is presumed that, in the gel particle measurement device in this embodiment, the gel particle detection by backward scattering immediately after the sample cuvet is more excellent than the detection by scattering in any of the directions, for the purpose of detecting produced minute particles as quickly as possible so as to capture particles that come out of nothing (phase transition called gelation).

Accordingly, the above-mentioned timing for phase transition is measured by adopting a detection system using backward scattering, for the purpose of quickly detecting minute particles emerging due to the phase transition by a limulus reagent with good sensitivity.

In summary, a system for detecting a backscattered light component in the scattered light generated by the emergence of minute particles is excellent in the following two points. That is, small particles can be detected quickly, and scattered light can be detected without absorption by a solvent in which particles are floating. Further, basically, it is not necessary to set an optical path through which incident light from the incident light source passes, and hence, it is also one of the excellent points that a mechanism of the device can be further simplified.

The present invention is hereinafter described in more detail based on embodiments illustrated in the attached drawings.

First Embodiment

A gel particle measurement device according to a first embodiment of the present invention includes a sample cuvet 100 into which a sample containing an endotoxin is injected, and measures the endotoxin concentration as a target substance in the sample, for example, through a gelation reaction using a limulus reagent.

Gel Particle Measurement Device

In this embodiment, the gel particle measurement device is configured as illustrated in FIG. 5.

In FIG. 5, the sample cuvet 100 is set on a predetermined measurement stage, and in this embodiment, the sample cuvet 100 is placed in a thermostatic chamber 115 so that the mixed solution W including the sample S and a reagent (not shown) is placed under a constant thermostatic environment (for example, 37° C.), thereby keeping a measuring condition constant.

In addition, reference symbol 120 represents a stirring-driving device for driving a magnetic stirrer bar 121 in the sample cuvet 100 so as to stir the mixed solution W in the sample cuvet 100, and the stirring-driving device 120 is structured so that, for example, a constant stirring state is provided to the mixed solution W, to thereby inhibit the entire mixed solution W from being gelating while stirring the mixed solution W homogeneously.

In particular, in this example, the stirring-driving device 120 is configured as a stirring-driving source (magnetic stirrer) to apply its stirring force due to a magnetic force to the stirrer bar 121 which is formed of a magnetic material and built in the bottom wall of the sample cuvet 100.

In addition, reference symbol 130 represents a laser light source which is installed outside the side peripheral wall of the sample cuvet 100 and emits coherent light.

Figure 6A:
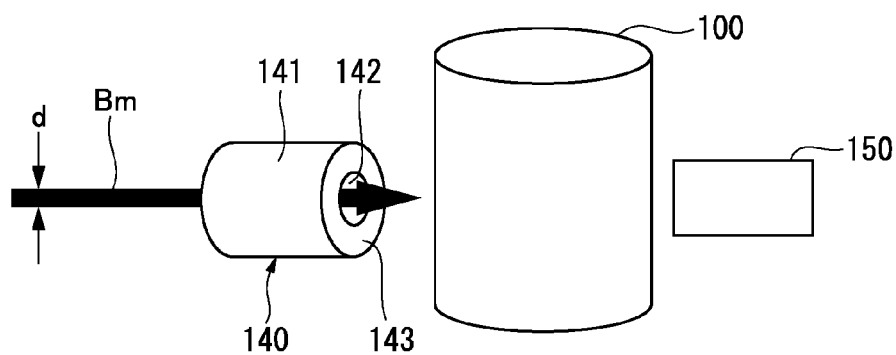
FIG. 6A is an explanatory diagram illustrating a configuration example of a laser light source and a backscattered light detector used in the first embodiment.
Figure 6B:
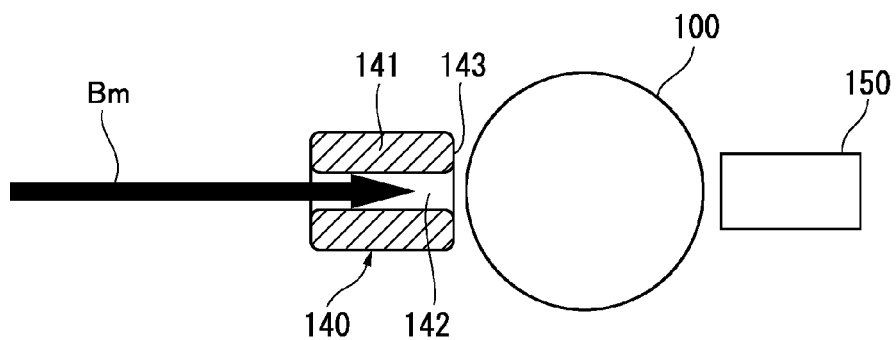
FIG. 6B is an explanatory partial cross-sectional plan view of FIG. 6A.

In this example, coherent light Bm from the laser light source 130 is, as illustrated in FIGS. 6A and 6B, travels along a route that runs across the near-diameter line of the sample cuvet 101, and a diameter d of the light is set to a value (for example, about 5 to 20 μm) sufficiently larger than the diameter (for example, about 0.2 to 2 μm) of each of the produced gel particles.

Further, reference symbol 140 represents a backscattered light detector provided outside the sample cuvet 100 on the same side on which the laser light source 130 is provided, the backscattered light detector 140 detecting a backscattered light component, which returns toward the laser light source 130, in the irradiation light Bm from the laser light source 130 scattered by the gel particles produced in the mixed solution in the sample cuvet 100.

In this example, the backscattered light detector 140 includes a cylindrical detector body 141 in which a passage hole 142 is opened at the center. The passage hole 142 of the detector body 141 allows irradiation light emitted from the laser light source 130 into the sample cuvet 100 to pass therethrough. A ring-shaped detecting surface 143 is provided on the detector body 141 so as to be opposed to a side peripheral wall outer surface of the sample cuvet 100, and further, a light-receiving element (not shown) such as a photodiode capable of sensing scattered light detected by the ring-shaped detecting surface 143 is incorporated into a part of the detector body 141.

In this case, the detection accuracy of the backscattered light detector 140 is set to such a degree as to detect a change in backscattered light quantity caused by the presence or absence of one to several gel particles in a passage area of the irradiation light Bm from the laser light source 130.

Although the ring-shaped detecting surface 143 of the backscattered light detector 140 may be placed in contact or in no contact with the side peripheral wall outer surface of the sample cuvet 100, it is preferred to place the ring-shaped detecting surface 143 in contact with the side peripheral wall outer surface from the viewpoint of keeping a satisfactory detection performance of a backscattered light component.

Further, in this embodiment, a stray light removing member 150 is provided outside the sample cuvet 100 and on an opposite side of the laser light source 130 with respect to the sample cuvet 100.

The stray light removing member 150 is configured so that a light absorbing member is provided correspondingly to a region of the sample cuvet 100 in which the irradiation light Bm emitted from the laser light source 130 into the sample cuvet 100 to pass through the sample cuvet 100 directly reaches a peripheral wall on the opposite side of the sample cuvet 100, and a peripheral region thereof.

The reason for providing the stray light removing member 150 in a part of the sample cuvet 100 as described above is as follows. That is, a scattered light component except a back-scattered light component returning toward the laser light source 130 in the irradiation light from the laser light source 130 scattered, for example, by gel particles, or a transmitted light component directly passing through the periphery of the produced gel particles can be stray light components reflected from the inner wall of the sample cuvet 100 and directed to the backscattered light detector 140. Of those, in particular, a stray light component having high directivity is a transmitted light component and a scattered light component directed in the same direction as that of the transmitted light component, and hence, the stray light removing member 150 is provided at a position corresponding to these light components.

Figure 8:
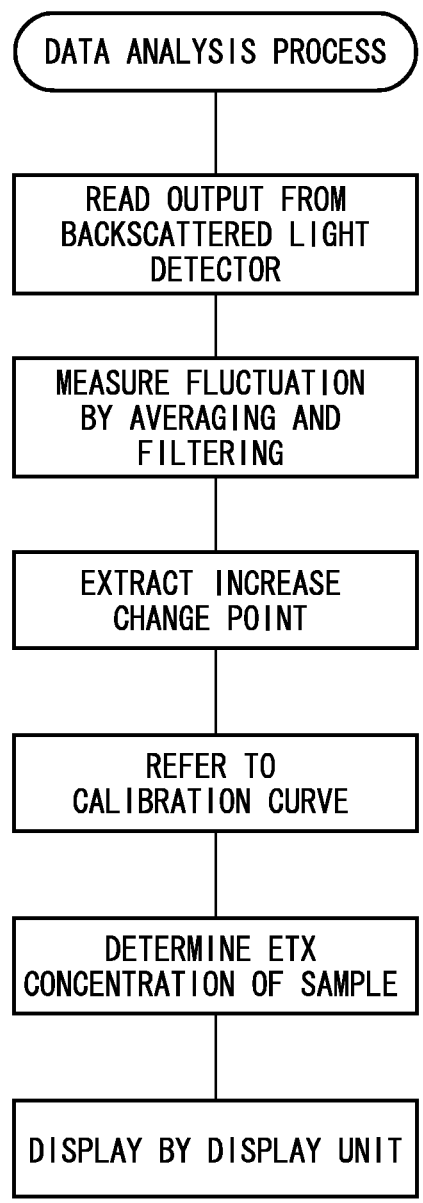
FIG. 8 is a flowchart illustrating an example of a data analysis process of the gel particle measurement device according to the first embodiment.

Reference symbol 160 represents a data analysis device which takes in a detection output from the backscattered light detector 140 and carries out such a data analysis process as illustrated in FIG. 8, for example. Reference symbol 170 represents a display unit for displaying the results of the analysis performed with the data analysis device 160.

The data analysis device 160 is configured of a computer system including a CPU, a ROM, a RAM, an I/O interface, and the like. For example, a data analysis process program illustrated in FIG. 8 is preliminarily installed in the ROM, and the data analysis process program is executed with the CPU based on the detection output from the backscattered light detector 140.

Note that, the detection output from the backscattered light detector 140 is, for example, subjected to current-voltage conversion in an amplifier (not shown) before subjected to AD conversion in an AD converter, and is taken into the data analysis device 160.

(Configuration Example of Sample Cuvet)

Next, a configuration example of the sample cuvet 100 used in this embodiment and an example of introducing a stirrer bar 121 and a sample S into the sample cuvet 100 are described in detail with reference to FIGS. 7A and 7B.

Figure 7B:
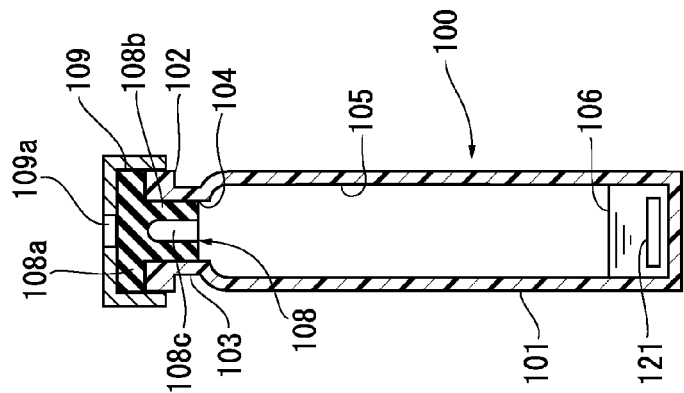
FIG. 7B is an explanatory cross-sectional view of FIG. 7A.
Figure 7A:
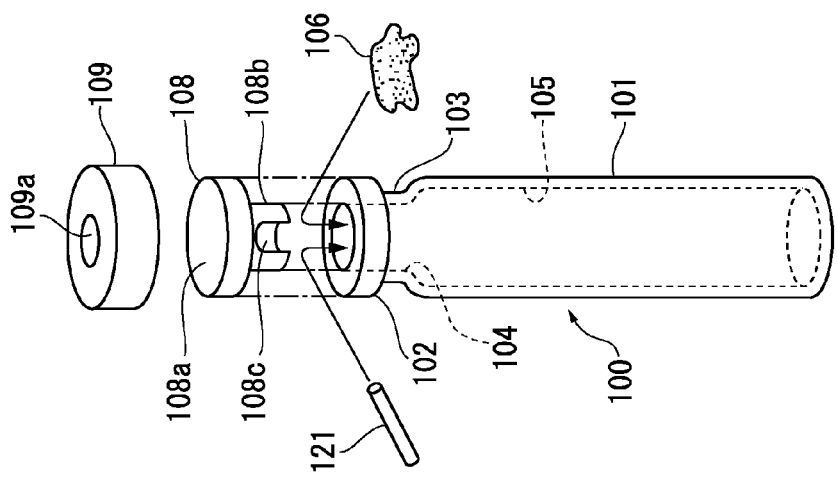
FIG. 7A is an exploded perspective view illustrating a sample cuvet used in the first embodiment.

In FIGS. 7A and 7B, the sample cuvet 100 is formed of, for example, a bottomed cylindrical container 101 that is integrally molded with a glass material and has a circular shape in a lateral cross-section with an upper part opened. In an upper part of the cylindrical container 101, a flange portion 102 is formed, and a constricted portion 103 is formed below the flange portion 102. A small diameter hole portion 104 is formed at the flange portion 102 and the constricted portion 103, and a large diameter space portion 105 larger in diameter than the small diameter hole portion 104 is formed inside the cylindrical container 101.

Then, in the sample cuvet 100, a sample containing an endotoxin and a reagent 106 causing a gelation reaction are accommodated, for example, in a freeze-dried powder shape in advance sterilely without an endotoxin (generally referred to as "endotoxin-free" or "pyrogen-free"), and the stirrer bar 121 using a magnetic material is accommodated in advance.

Further, a sealing stopper 108 made of an elastic material such as rubber is fitted in the small diameter hole portion 104 of the sample cuvet 100. The sealing stopper 108 is formed into a substantially T-shape in cross-section. A head portion 108a of the sealing stopper 108 is placed on the flange portion 102 of the sample cuvet 100, and a leg portion 108h of the sealing stopper 108 is inserted in the small diameter hole portion 104 in close contact therewith. Note that, a part of the leg portion 108b of the sealing stopper 108 is provided with a cutout 108c.

Further, the flange portion 102 of the sample cuvet 100 and the head portion 108a of the sealing stopper 108 are covered with, for example, a cap-shaped holding cover 109 made of aluminum, and the holding cover 109 is fitted on a peripheral wall of the flange portion 102 of the sample cuvet 100 to surround and hold the sealing stopper 108 from an outside. Then, for example, at the center of the holding cover 109, a hole portion 109a is formed so as to face the head portion 108a of the sealing stopper 108.

Further, as illustrated in FIGS. 7A and 7B, the sample cuvet 100 accommodates the reagent 106 and the stirrer bar 121 under a state in which the small diameter hole portion 104 of the cylindrical container 101 is opened, and in this state, the sealing stopper 108 seals the small diameter hole portion 104 of the cylindrical container 101, and the sealing stopper 108 is covered with the holding cover 109.

The sample cuvet 100 is supplied to a user as an accessory or a measurement kit of a gel particle measurement device.

Then, as a method of introducing the sample S into the cylindrical container 101 of the sample cuvet 100 of this embodiment, for example, there is a method of perforating the sealing stopper 108 through use of the hole portion 109a of the holding cover 109 with a perforation tool (not shown) such as an injection needle, and injecting the sample S into the cylindrical container 101 with an injector (not shown) through the perforated hole. Further, in order to facilitate the introduction of the sample S, the sealing specification of the sealing stopper 108 may be set so that the inside of the cylindrical container 101 keeps a predetermined negative pressure level with respect to the atmospheric pressure.

Next, operation of the gel particle measurement device according to this embodiment is described.

In this embodiment, as illustrated in FIG. 5, the sample S containing an endotoxin is injected into the sample cuvet 100, and a start switch (not shown) is switched on, leading to the start of measurement sequence by the gel particle measurement device.

In the measurement sequence, the stirrer bar 121 is caused to rotate by the stirring-driving device 120 to stir the mixed solution W including the sample S and the limulus reagent in the sample cuvet 100. Thus, the entire mixed solution W is stirred uniformly and is inhibited from being gelated.

Further, in the measurement sequence, the mixed solution W in the sample cuvet 100 is irradiated with the coherent light Bm from the laser light source 130, a backscattered light component directed toward the laser light source 130 in the light scattered in the mixed solution W is detected with the backscattered light detector 140, and a detection output from the backscattered light detector 140 is taken into the data analysis device 160

On the other hand, in the mixed solution W of the sample cuvet 100, the stimulation of the endotoxin is delivered to the limulus reagent, a limulus response illustrated in FIG. 3 takes place, and the gel particles G are sequentially produced while the gelation of the entire mixed solution W is inhibited.

In this embodiment, a time when, for example, one gel particle G is produced in a passage area of the coherent light Bm from the laser light source 130 is grasped as a starting point of the production of the gel particle G, which leads to the timing of a phase transition point of the mixed solution W from a sol phase to a gel phase.

In the reaction process described above, the data analysis device 160, for example, as illustrated in FIG. 8, reads the detection output from the backscattered light detector 140 as data of the amount of scattered light (digital data), and then averaging and filtering processes are carried out to measure the fluctuation component in the data of the amount of scattered light.

Next, the changing point to increase (corresponding to $P_2$ of Step II in FIG. 2C) of the data of the amount of the scattered light detected by the backscattered light detector 140 is extracted based on the fluctuation component in the data of the amount of scattered light, and the endotoxin concentration (ETX concentration) in the sample S is determined by referring to a preliminarily defined calibration curve. The result is displayed on the display unit 170.

The calibration curve in this example shows a relationship between the endotoxin concentration (ETX concentration) and the threshold of a time to the changing point to increase of the data of the amount of scattered light. The endotoxin concentration (ETX concentration) is determined based on a correlation between the time to the changing point to increase of the data of the amount of scattered light and the calibration curve. Further, the display unit 170 is switched to display data such as time-series data of the amount of scattered light and time-series measurement data of the fluctuation component in the data of the amount of scattered light, in addition to displaying the endotoxin concentration (ETX concentration).

(Example of Created Calibration Curve)

An example of a created calibration curve adopted in this embodiment is hereinafter described.

A change in scattering luminosity (data of the amount of scattered light) is checked by the backscattered light detector 140 in the gel particle measurement device, with respect to limulus reagents when samples containing various endotoxin concentrations (for example, 10, 1, and 0.1 pg/ml) are added, defining predetermined experimental conditions, for example, as follows, using the gel particle measurement device according to the first embodiment.

The experimental conditions used in this example are as follows.

Laser light source 130: red light or blue light
Backscattered light detector 140: photodiode
Number of rotations of stirrer bar 121: 1,000 rpm
Thermostatic condition: 37° C.

Figure 9A:
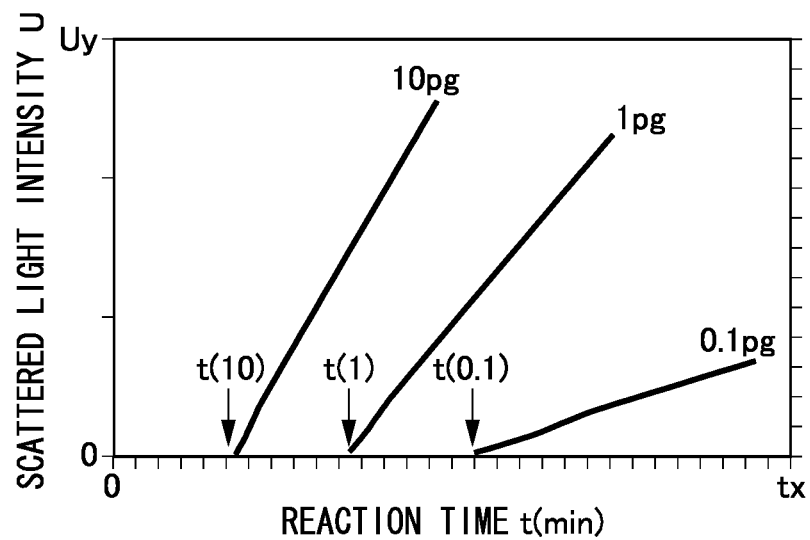
FIG. 9A is an explanatory graph showing a detection example of gel particles obtained by irradiating a sample having a known endotoxin concentration with backscattered measuring light.

FIG. 9A is a graph prepared by plotting the values of the scattered light intensity at time course for each sample of the endotoxin concentrations of 10 pg/ml, 1 pg/ml, and 0.1 pg/ml. A vertical axis of FIG. 9A represents scattered light intensity U (maximum scattered light intensity scale in the graph is represented by Uy), and a horizontal axis of FIG. 9A represents a reaction time (maximum reaction time scale in the graph is represented by tx [for example, 100 min]).

In FIG. 9A, any of the changes in the scattered light intensities for respective conditions shows the tendency that the portion kept at a constant level of nearly 0 increases after a certain time passes. The changing point to increase of each of the scattered light intensities corresponds to the starting point of the production of gel particles (timing of phase transition of the sample containing an endotoxin from a sol phase to a gel phase), and is estimated to mean the increase of light in amount owing to the starting time of gelation.

In order to determine the starting time of gelation, in this embodiment, in the graph of FIG. 9A, there was manually determined the intersection point between a straight line obtained by approximating the portion in which the scattering luminosity is constant (generally, 0) and a straight line obtained by approximating the changing portion in which the scattered light intensity is increasing, to thereby determine each of the starting times of gelation (reaction times) t(10), t(1), and t(0.1).

Figure 9B:
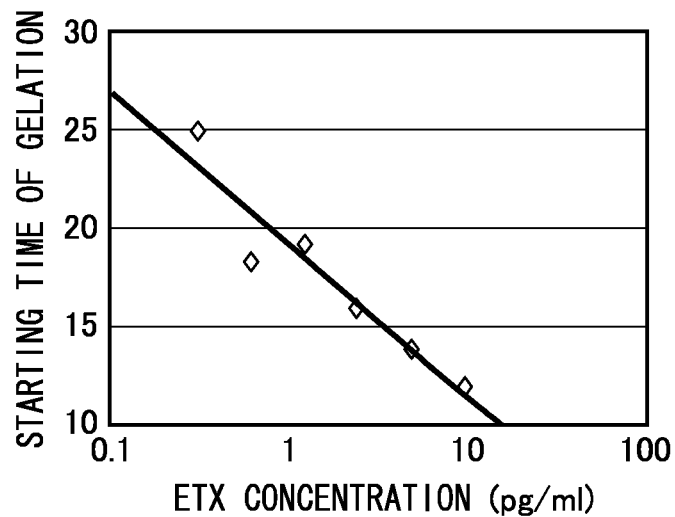
FIG. 9B is an explanatory graph showing an example of a calibration curve created through use of a result of FIG. 9A.

Further, in this embodiment, the values of the starting times of gelation t(10), t(1), and t(0.1), which were obtained from the graph of FIG. 9A, were used to prepare a calibration curve (see FIG. 9B).

In FIG. 9B, the calibration curve is prepared by plotting values of respective starting times of gelation, taking the ETX concentration (logarithmically converted) as the endotoxin concentration in the X-axis and taking the staring time of gelation in the Y-axis, and by drawing a straight line by a minimum square method with respect to these values. At this time, a linear relationship is obtained in the values of the starting times of gelation with respect to the sample of each endotoxin concentration, and thus, a high correlation showing a correlation coefficient is exhibited.

By the way, an example of the calibration curves obtained in this embodiment is as follows.

| Endotoxin concentration (pg/ml) | Starting time of gelation (min.) |
|---|---|
| 10 pg/ml:t(10) | = 12 (min.) |
| 1 pg/ml:t(1) | = 20 (min.) |
| 0.1 pg/ml:t(0.1) | = 27 (min.). |

For comparison, an endotoxin kit (gelation reaction measurement device) manufactured by Wako Pure Chemical Industries, Ltd. and adopting a turbidimetric assay was used, and endotoxin concentrations and gelation times were investigated. The following results were provided.

| Endotoxin concentration (pg/ml) | Gelation time (min.) |
|---|---|
| 10.0 | 18.0 |
| 1.0 | 41.8 |
| 0.5 | 56.3 |
| 0.1 | 123.7 |

As described above, in this embodiment, the gel particle measurement device stirs the mixed solution W including the sample S and the limulus reagent under a predetermined thermostatic environment, detects a backscattered light component returning backward toward the laser light source 130 in the irradiation light Bm partially blocked and scattered due to the emergence of the gel particles G made of Coagulin particles produced in the mixed solution W, and captures the starting time of gelation.

That is, this embodiment adopts a system of detecting a backscattered light component, and is effective for grasping a starting point of the production of gel particles, as compared with other systems of detecting a scattered light component.

Particularly, in this example, in order to obtain high sensitivity of detection accuracy of the backscattered light detector 140, coherent strong light such as laser light is used, and in order to detect a minute change, in a change at low density, stray light is removed by the stray light removing member 150 so that scattered light except backscattered light and transmitted light directly passing through the periphery of the gel particles in the light scattered particularly is not directed toward the backscattered light detector 140 as the stray light. Thus, only a backscattered light component scattered by the gel particles in the irradiation light Bm from the laser light source 130 enters the backscattered light detector 140, and a change in backscattered light is correspondingly detected reliably.

Modified Embodiment

Figure 10A:
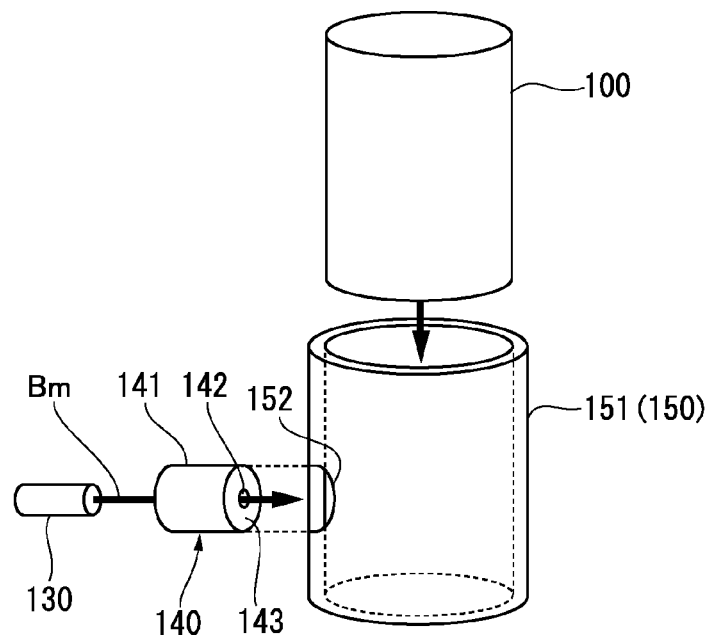
FIGS. 10A and 10B are explanatory views illustrating a modified embodiment of the gel particle measurement device according to the first embodiment.

In this embodiment, the stray light removing member 150 is arranged outside the sample cuvet 100 and on an opposite side of the laser light source 130 with respect to the sample cuvet 100. However, the present invention is not limited thereto. For example, as illustrated in FIG. 10A, a tubular cover 151 may be set so as to surround the periphery of the sample cuvet 100, the inner surface of the tubular cover 151 may be covered with, for example, a black light absorbing member and a fitting hole 152 for mounting the backscattered light detector 140 may be opened in a part of the tubular cover 151, the backscattered light detector 140 may be mounted through the fitting hole 152, and the irradiation light Bm from the laser light source 130 may be allowed to pass through the passage hole 142 of the backscattered light detector 140.

Further, in this embodiment, although the sample cuvet 100 is formed of a transmissive material, transmission of light in the mixed solution W in the sample cuvet 100 is hardly required. Therefore, as long as part of the sample cuvet 100 corresponding to setting positions of the laser light source 130 and the backscattered light detector 140 is set as an incident portion having transmissive property, the other parts of the sample cuvet 100 may be formed of a non-transmissive material or may be coated with a non-transmissive coating.

Figure 10B:
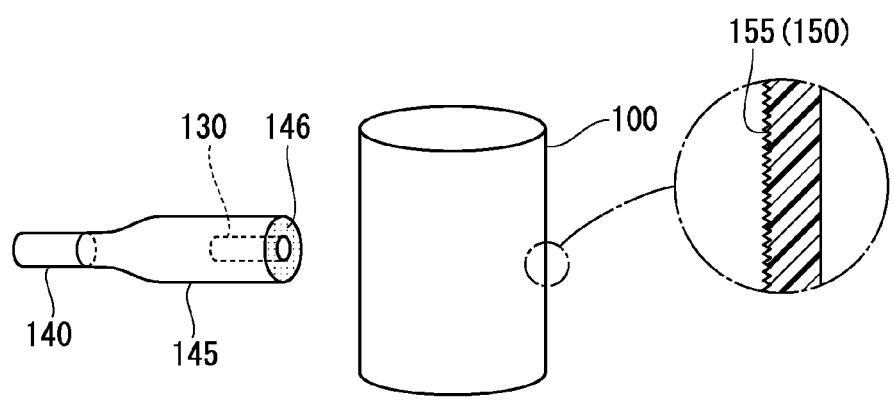

Further, in this embodiment, although the laser light source 130 and the backscattered light detector 140 are configured as separate units, for example, as illustrated in FIG. 10B, a number of light-transmissive glass fibers 145 as a light guiding member may be bound so as to surround the periphery of the laser light source 130, one end of each glass fiber 145 on the sample cuvet 100 side may be allowed to function as a light introduction surface 146, the backscattered light detector 140 may be provided so that a detection surface is placed so as to be opposed to the other end of each glass fiber 145, and an optical detection unit may be configured integrally, using the laser light source 130, the backscattered light detector 140, and the glass fibers 145 as a light guiding member.

Further, the stray light removing member 150 is not limited to a form in which the stray light removing member 150 is provided outside the sample cuvet 100. For example, as illustrated in FIG. 10B, a minute rough surface 155 may be formed on an inner wall circumferential surface of the sample cuvet 100 as the stray light removing member 150, and a stray light component in the irradiation light emitted from the laser light source 130 may be randomly reflected from the minute rough surface 155 to be attenuated.

Note that, although the stray light removing member 150 is provided in this embodiment, it is not necessarily required to use the stray light removing member 150. For example, the degree of influence of a stray light component may be actually measured in advance through use of a sample of a known endotoxin concentration, and based on the actually measured value, for example, the stray light component actually measured from a detection output from the backscattered light detector 140 may be corrected.

Further, in this embodiment, the gel particle measurement device with respect to the sample cuvet 100 for one analyte (sample S) is shown. However, under a request that a plurality of analytes (samples) be treated simultaneously, for example, a multi-sample cuvet in which a plurality of sample cuvets 100 are integrated may be prepared and the laser light source 130 and the backscattered light detector 140 may be arranged correspondingly to each sample cuvet so that a plurality of analytes (samples) can be measured simultaneously.

Further, although the first embodiment discloses that a substance to be measured is an endotoxin, the present invention is not limited thereto. For example, a substance to be measured may be a β-D-glucan, using the same measurement hardware and the same or similar limulus reagent.

Second Embodiment

FIG. 11 illustrates main portions of a gel particle measurement device of a second embodiment to which the present invention is applied. Note that, the same constituent elements as those of the first embodiment are denoted by the same reference symbols as those in the first embodiment, and the detailed description thereof is omitted.

In FIG. 11, substantially in the same way as in the first embodiment, the gel particle measurement device includes the laser light source 130 outside the sample cuvet 100, and the backscattered light detector 140 is set on the same side as the laser light source 130. Unlike the first embodiment, however, for example, a second scattered light detector 180 is set outside the sample cuvet 100 and on an opposite side of the backscattered light detector 140 (corresponding to the first scattered light detector) with respect to the sample cuvet 100, detection outputs of the second scattered light detector 180 as well as the first scattered light detector 140 are taken into the data analysis device 160, a starting point of the production of gel particles is determined in the same way as in the first embodiment based on the detection output from the first scattered light detector 140, and production state information of gel particles (for example, the production amount of gel particles) at points except the starting point of the production of gel particles is determined based on the detection output (forward scattered light output) of the second scattered light detector 180.

In this example, in the second scattered light detector 180, a scattered light component except the backscattered light component is detected. However, there is a possibility that, for example, a transmitted light component may also be detected in the second scattered light detector 180, and hence, in the case where it is desired to remove a transmitted light component as an object to be detected of the second scattered light detector 180 for data analysis, a deflection filter 190 may be set to remove the transmitted light component, utilizing the fact that the scattered light component and the transmitted light component are shifted in phase.

Further, in the case where the deflection filter 190 is not used, the second scattered light detector 180 detects a scattered light component containing a transmitted light component. In this case, the scattered light component may be analyzed considering that a transmitted light component is included on the data analysis device 160 side, or the scattered light component may be analyzed after correction is made so as to remove the transmitted light component on the data analysis device 160 side.

The second scattered light detector 180 basically detects a scattered light component alone or together with a transmitted light component. However, for example, when a deflection filter for removing a scattered light component is interposed, only the transmitted light component containing no scattered light component can also be analyzed.

Further, in this example, a starting point of the production of gel particles is determined through use of the detection output from the first scattered light detector 140, and production state information of gel particles at points except the starting point of the production of gel particles is determined through use of the second scattered light detector 180. However, the present invention is not limited thereto, and production state information of gel particles at points except the starting point of the production of gel particles may be determined through use of both the detection outputs of the first scattered light detector 140 and the second scattered light detector 180. In this case, by using difference information of the detection outputs of the first scattered light detector 140 and the second scattered light detector 180, for example, properties of a sample solvent can be calibrated from a non-specific increase in turbidity and generation of stray light caused by scattered light and a sample, or the degree of attenuation caused by the absorption of scattered light derived from a sample solvent, with the result that production state information of gel particles can be analyzed in more detail.

Note that, in this embodiment, although the second scattered light detector 180 is set on an opposite side of the first scattered light detector 140 with respect to the sample cuvet 100, the present invention is not limited thereto, and the second scattered light detector 180 may be set in an arbitrary place as long as the place is different from that of the first scattered light detector 140. For example, when the second scattered light detector 180 is set at a place shifted by 90° in a circumferential direction of the sample cuvet 100 with respect to the first scattered light detector 140, sideward scattered light illustrated in FIG. 4B can be detected.

EXAMPLES

Example 1

In Example 1, a plurality of samples obtained by adding an endotoxin at a known concentration to water or a whole blood solution are prepared, and a change in backscattered light in each of the samples is measured in a time series through use of a model device embodying the gel particle measurement device according to the first embodiment.

Samples of this example are as described below.

Sample I=sample obtained by adding 10 pg/ml of a standard endotoxin to water

Figure 12A:
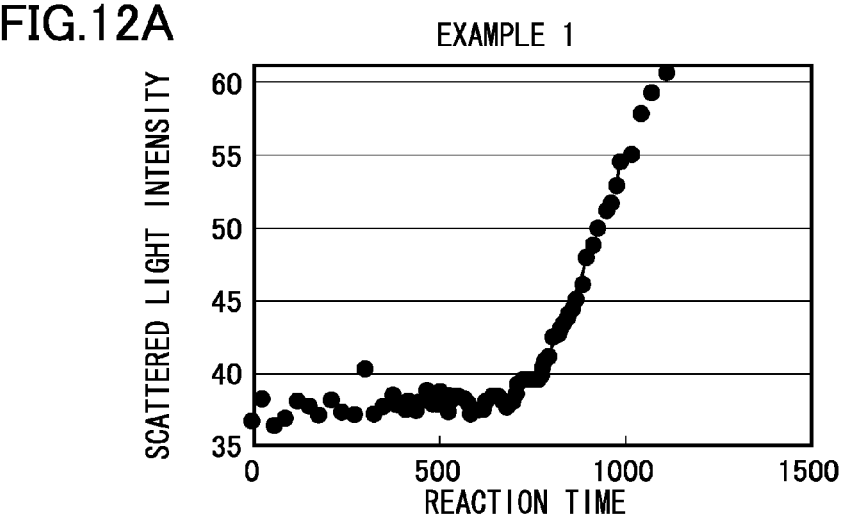
FIG. 12A is an explanatory graph showing an example of actually measured data obtained by irradiating a water sample having a standard endotoxin added thereto with backscattered measuring light through use of a gel particle measurement device according to Example 1.
Figure 13A:
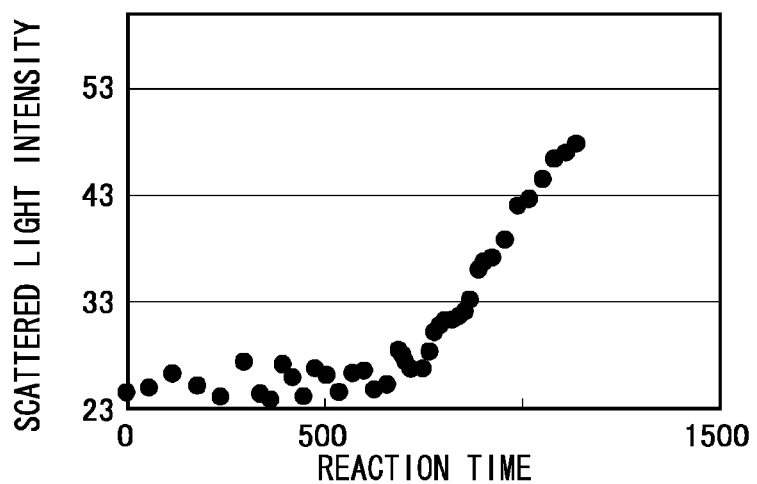
FIG. 13A is an explanatory graph showing an example of actually measured data obtained by irradiating a sample, which is obtained by adding a standard endotoxin to a clinical hemolyzed whole blood sample, with backscattered measuring light through use of the gel particle measurement device according to Example 1.

Sample II=sample obtained by adding 10 pg/ml of a standard endotoxin to a hemolyzed whole blood sample Sample III=sample obtained by adding no endotoxin to a hemolyzed whole blood sample The results of Samples I to III are shown in FIGS. 12A, 13A, and 14A.

Note that, a vertical axis of each figure represents a relative scattered light intensity, and a horizontal axis thereof represents a time (sec.).

Comparative Example 1

In Comparative Example 1, a change in forward scattered light directed forward on an opposite side of backscattered light is measured in samples similar to Samples I, II, and III used in Example 1 in a time series through use of a model device (including the deflection filter 190) embodying the gel particle measurement device according to the second embodiment.

Figure 12B:
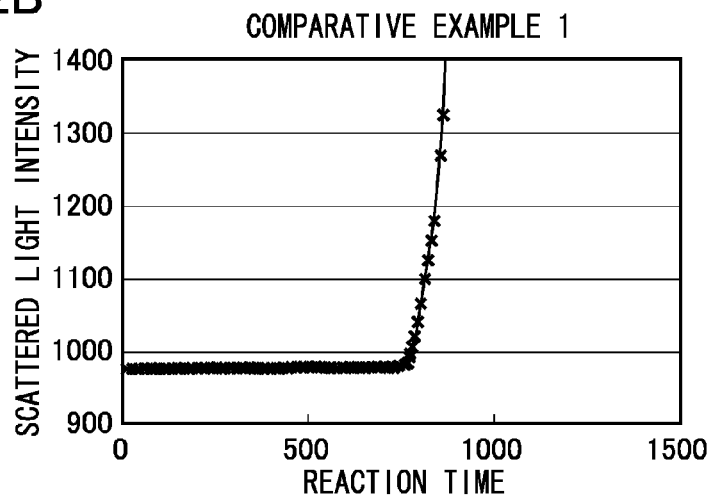
FIG. 12B is an explanatory graph showing an example of actually measured data obtained by irradiating a water sample having a standard endotoxin added thereto, which is similar to that of FIG. 12A, with forward scattered measuring light together with backscattered measuring light through use of a gel particle measurement device according to Comparative Example 1.
Figure 13B:
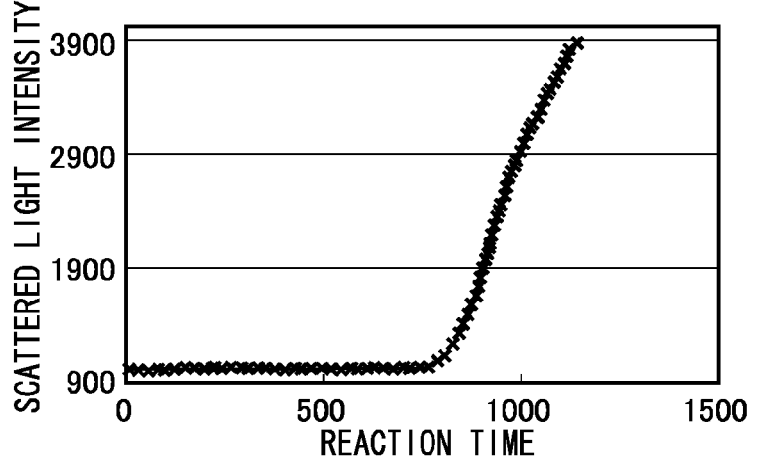
FIG. 13B is an explanatory graph showing an example of actually measured data obtained by irradiating a sample, which is obtained by adding a standard endotoxin to a clinical hemolyzed whole blood sample and is similar to that of FIG. 13A, with forward scattered measuring light together with backscattered measuring light through use of the gel particle measurement device according to Comparative Example 1.

The results of Samples I to III are shown in FIGS. 12B, 13B, and 14B.

Note that, a vertical axis of each figure represents a relative scattered light intensity, and a horizontal axis thereof represents a time (sec.).

Comparative Example 2

In Comparative Example 2, a change in transmitted light (in this example, including forward scattered light) directed forward on an opposite side of backscattered light is measured in samples similar to Samples I, II, and III used in Example 1 in a time series through use of a model device embodying the gel particle measurement device according to the second embodiment.

Figure 12C:
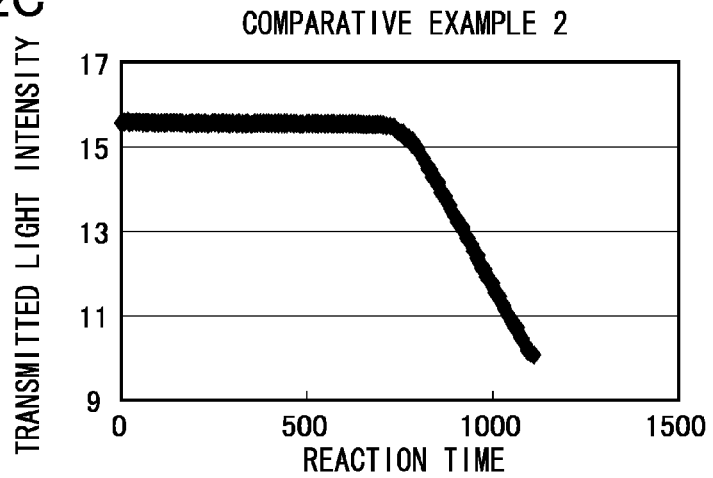
FIG. 12C is an explanatory graph showing an example of actually measured data obtained by irradiating a water sample having a standard endotoxin added thereto, which is similar to that of FIG. 12A, with forward transmitted light together with backscattered measuring light through use of a gel particle measurement device according to Comparative Example 2.
Figure 13C:
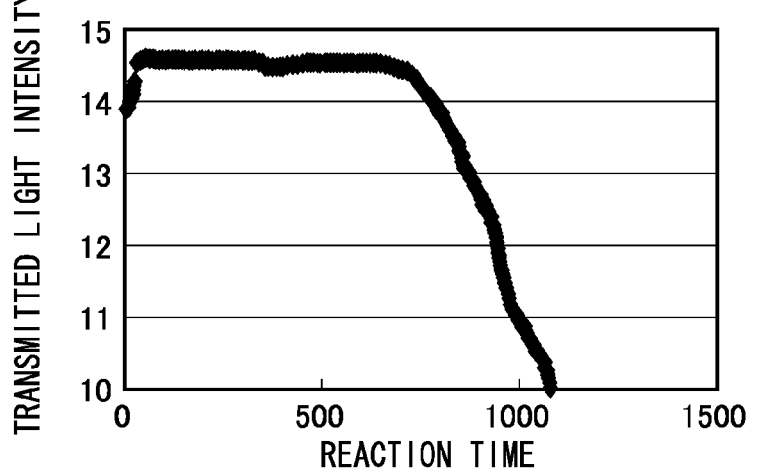
FIG. 13C is an explanatory graph showing an example of actually measured data obtained by irradiating a sample, which is obtained by adding a standard endotoxin to a clinical hemolyzed whole blood sample and is similar to that of FIG. 13A, with forward transmitted light together with backscattered measuring light through use of the gel particle measurement device according to Comparative Example 2.

The results of Samples I to III are shown in FIGS. 12C, 13C, and 14C.

Note that, a vertical axis of each figure represents a relative scattered light intensity, and a horizontal axis thereof represents a time (sec.).

Comparison between Example 1 and Comparative Examples 1 and 2

When Example 1 is compared with Comparative Example 1, compared with the timing of phase transition of a sample based on a decrease in transmitted light in Comparative Example 2, any starting time of production of gel particles (increase change point of scattering luminosity) corresponding to the timing of phase transition of a sample by forward scattered light according to Comparative Example 1 tends to be delayed (about 10 to 40 seconds) in detection start from a starting time of production of gel particles (increase change point of scattering luminosity) corresponding to the timing of phase transition in a sample by backscattered light according to Example 1.

Further, considering data on the measurement of an endotoxin at a low concentration equal to that of a clinical sample itself (see FIGS. 14A to 14C), for example, in the case of Comparative Example 2, it is difficult to perform quantification based on a transmitted light quantity due to the obstacles such as unknown precipitation and aggregation in Sample III, and a reaction of a mixed solution system in Sample III as well as a starting time of production of gel particles cannot be determined. However, a starting time of production of gel particles is detected remarkably according to the detection system using forward scattered light of Comparative Example 1.

However, according to the detection system using forward scattered light of Comparative Example 1, a scattered light component is attenuated in the course of the passage through a sample solution, and hence, the detection timing of the production of gel particles is delayed compared with that of Example 1 (14A), and the detection timing with respect to the growth of gel particles is also delayed. As a result, it is apparent that the detection timing is delayed remarkably (about 200 to 300 seconds) in the detection system using forward scattered light, compared with that in the detection system using backscattered light, and the superiority of the system using backscattered light is understood all the more. This tendency is further conspicuous in a low endotoxin concentration (that is, a sample in which less gel particles are produced).

Example 2

This example is a specific example of an averaging process that is one of data analysis processes of the gel particle measurement device according to the first embodiment.

Figure 15A:
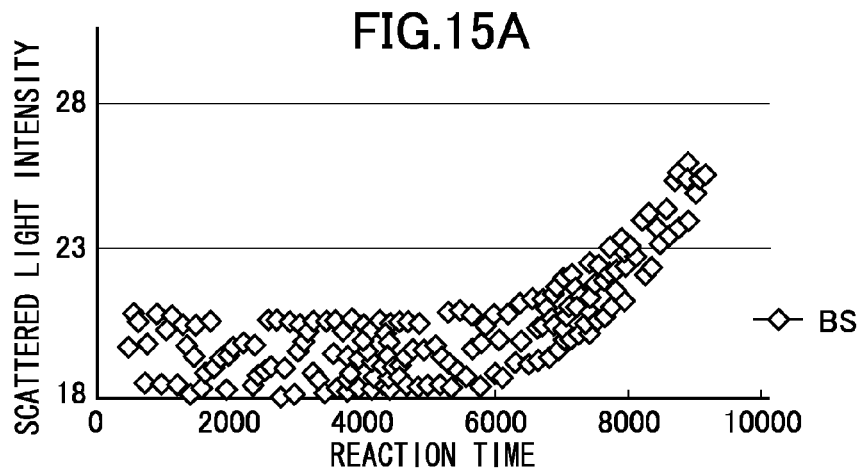
FIG. 15A is an explanatory graph showing an example of actually measured data obtained by irradiating a sample with backscattered measuring light through use of the gel particle measurement device according to Example 1.

FIG. 15A shows actually measured data (BS) prepared by plotting changes in backscattered light in the backscattered light detector 140 (corresponding to FIG. 14A).

Figure 15B:
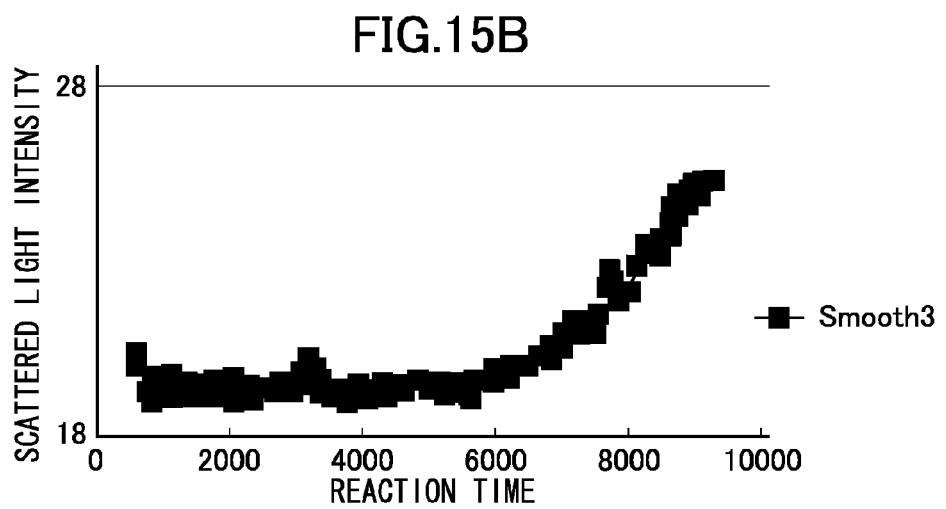
FIG. 15B is an explanatory graph showing an example of data obtained by subjecting the actually measured data of FIG. 15A to a smoothing process on a basis of three pieces of data.
Figure 15C:
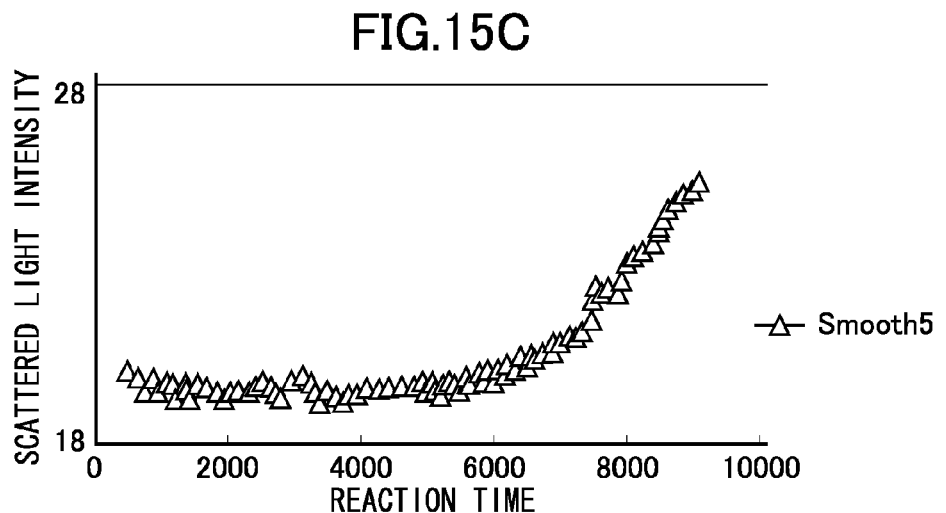
FIG. 15C is an explanatory graph showing an example of data obtained by subjecting the actually measured data of FIG. 15A to a smoothing process on a basis of five pieces of data.

FIG. 15B shows a smoothing process (Smooth 3) of averaging three points in the vicinity of the actually measured data in FIG. 15A, and FIG. 15C shows a smoothing process (Smooth 5) of averaging five points in the vicinity of the actually measured data in FIG. 15A.

It is understood that a data group in FIG. 15B is narrower than the actually measured data, and a data group in FIG. 15C is further narrower than the data group in FIG. 15B.

Accordingly, even when the actually measured data varies in a certain width, the actually measured data can be averaged by a desired smoothing process, and it is understood that the smoothing process is effective for a data analysis process.

Industrial Applicability

The present invention is widely applied to a measurement device in which a target substance capable of producing gel particles through a gelation reaction is to be measured, as well as a gel particle measurement device in which an endotoxin or a β-D-glucan is to be measured using a limulus reagent.

For example, the present invention can be applied to a blood-clotting reaction or an antigen-antibody reaction.

Figure 16:
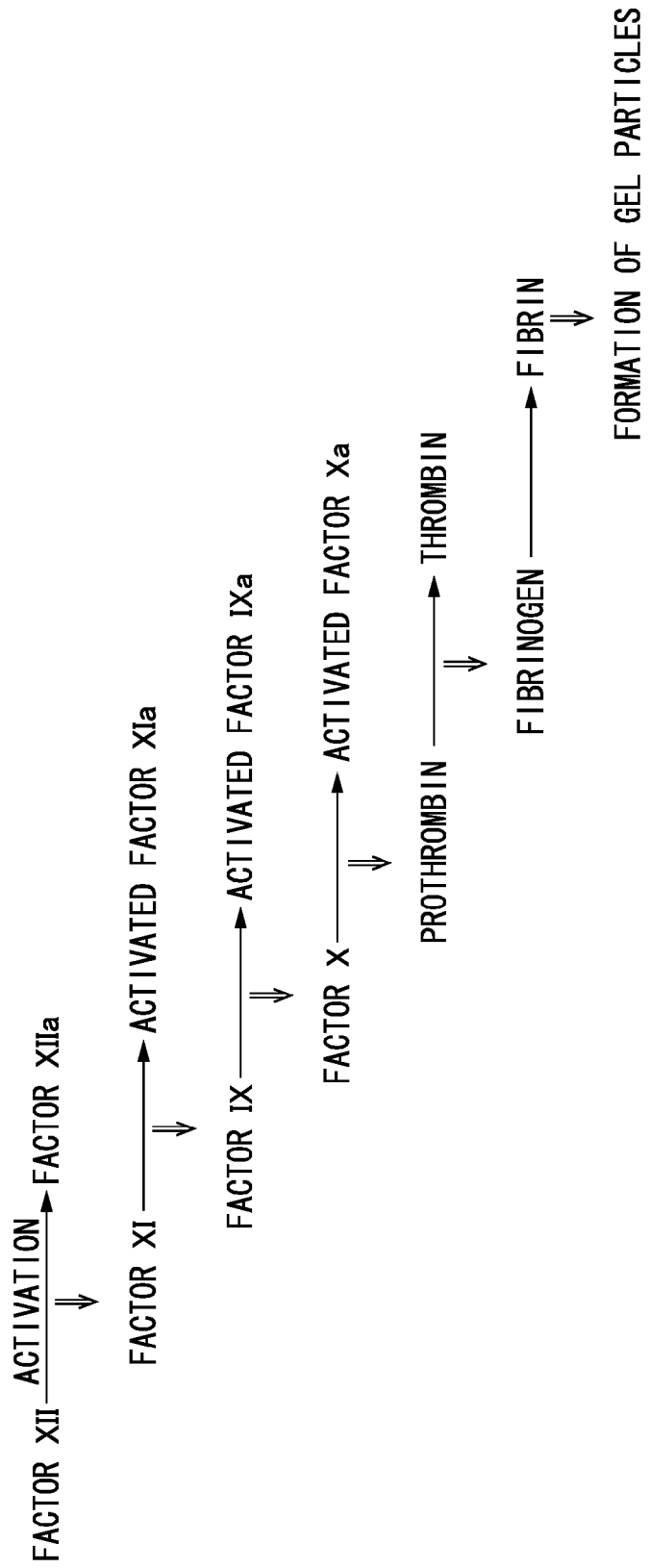
FIG. 16 is an explanatory diagram illustrating application examples of the present invention in a blood-clotting reaction.

Blood-clotting reaction (FIG. 16)

Prothrombin in blood plasma becomes thrombin through activation of various blood-clotting factors, and fibrin is aggregated.

For supplemental description, a coagulation system of blood plasma proceeds through the following initiation period, amplification period, and propagation period.

(Initiation Period)
(Extrinsic Pathway)

When a cell is damaged in a blood-clotting cascade, a tissue factor binds to factor VIIa (activated factor VII).

In this case, factor VIIa activates factor IX to produce factor Ixa. Further, factor IXa activates factor X to produce factor Xa.

(Intrinsic Pathway)

When blood comes into contact with a solid (for example, rock or sand) charged negatively, prekallikrein and a high-molecular-weight kininogen activate factor XII to produce factor XIIa. Further, factor XIIa activates factor XI to produce factor XIa. Further, factor XIa activates factor IX to produce factor IXa.

(Amplification Period)

Thrombin activates factor XI to produce factor XIa. Factor XIa activates factor IX to produce factor IXa. Further, thrombin itself activates factor V and factor VIII to produce factor Va and factor VIIIa, respectively. Further, thrombin activates blood platelet to bind factor XIa, factor Va, and factor VIIIa to the surface of blood platelet.

(Propagation Period)

Factor VIIIa and factor IXa bound to the surface of blood platelet activate factor X to be bound to the surface of blood platelet. Further, factor Xa and factor XIa bound to the surface of blood platelet change prothrombin to thrombin successively. Further, a large amount of thrombin decomposes fibrinogen in blood plasma to produce a fibrin monomer. The fibrin monomer is cross-linked with factor XIII to produce a fibrin polymer, which involves other blood cells to become a blood clot (scab).

In a living body, the above-mentioned reaction is useful for closing the wound through blood clotting, for example. However, on the other hand, when a minute aggregated clot is generated in blood stream, the clot becomes a blood clot to close various small blood vessels to cause serious clinical conditions such as brain ischemia, cardiac ischemia, and pulmonary embolism. Thus, clinical determination of "ease of aggregation" is important for predicting the generation of an aggregated clot. Conventionally, a prolonged aggregation time is measured based on the fear that "bleeding does not stop", but there is no estimated method of measuring "ease of blood clotting". It is expected that the degree of aggregation can be measured by mixing blood plasma diluted appropriately and a predetermined amount of a reagent (for example, ADP, collagen, or epinephrine) for promoting aggregation through the particle measuring method.

Therefore, in this example, a predetermined amount of ADP or the like is placed aseptically in the sample cuvet 100 together with the magnetic stirrer bar 121 to prepare the sample cuvet 100 subjected to treatment such as freeze drying. Blood plasma diluted appropriately in clinical practice is introduced into the sample cuvet 100 through the sealing stopper 108 in the upper part, and a generation time of an aggregated clot, that is, a starting time of gelation is measured with a gel particle measurement device similar to that of the first embodiment, with the result that the degree of an aggregation ability can be measured.

Antigen-antibody Reaction (FIG. 17)

Figure 17A:
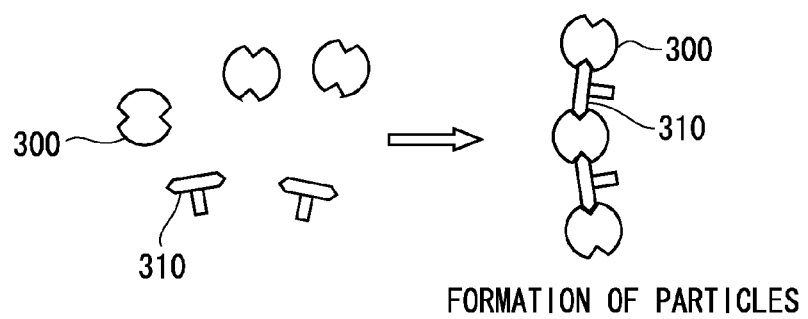
FIGS. 17A and 17B are explanatory views illustrating application examples of the present invention in an antigen-antibody reaction.

As illustrated in FIG. 17A, specific antibodies 310 against various antigens 300 associate to accelerate inactivation of the antigens 300 as insoluble precipitates and defend a living body. Meanwhile, when the specific antibodies 310 are prepared in advance, the amount of precipitates to be generated are proportional to that of the antigens 300 that are present, and hence, various methods of quantifying the antigens 300 have been proposed through use of the above-mentioned phenomenon. However, it takes a long time for precipitation (or accelerating the antigen-antibody association), and hence, various detecting methods and sensitive detection devices have been developed. When the precipitate formation in an antigen-antibody reaction is taken as particle formation of gelation, a gel particle measurement device for forming particles stably and measuring the particles is considered to be applicable.

Figure 17B:
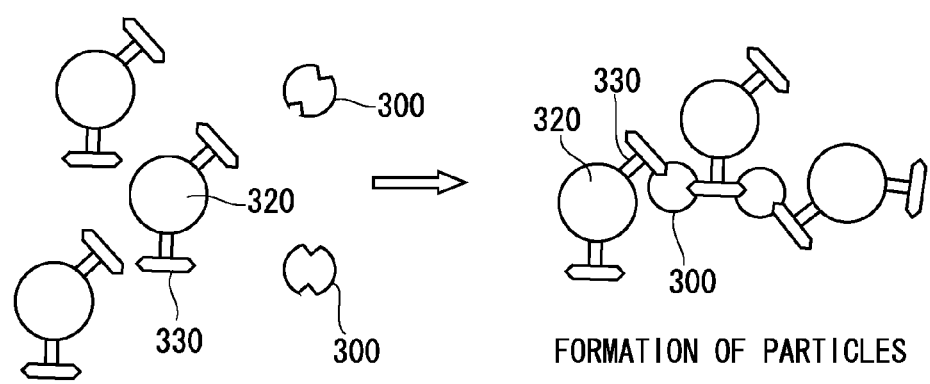

Above all, as illustrated in FIG. 17B, in a detection reaction of a type involving binding the antibodies 330 to microbeads 320 or the like made of a resin or the like and causing an antigen-antibody reaction to occur between the surface of the beads and the antigen 300, the precipitate formation can be easily found by a change in pattern of particle formation, and this can also be applied to the method thereof.

Therefore, a predetermined amount of an antibody 330 or a solution of the antibody bound to the microbeads 320 is placed aseptically in the sample cuvet 100 together with the magnetic stirrer bar 121. In this case, it is necessary to hold the activity of the antibody 330, and hence it is considered to be better to preserve the antibody 330 as a solution instead of a freeze-dried state. In the case of performing measurement, a solution to be detected such as blood plasma diluted in a predetermined manner is introduced into the sample cuvet 100 through the sealing stopper 108 in the upper part, and the generation rate of aggregated clots by the antigen-antibody reaction is measured, for example, with the gel particle measurement device of the first embodiment. In particular, a decrease rate of transmitted light is measured so as to grasp the rate of gel particle production.

The methods of using the following three reactions: an endotoxin active reaction, a blood-clotting reaction, and an antigen-antibody reaction described in the first embodiment are common in grasping a reaction in which molecules dissolved homogeneously in water associate to become insoluble particles and quantifying the particles. When the soluble molecules become insoluble, a reaction bias (reaction molecules are locally insufficient around an enzyme to be the center of the reaction) phenomenon occurs. In order to allow the reaction to proceed correctly and measure the rate thereof, this bias needs to be "zero" theoretically. A solution to the problem is "stirring". The measurement method mainly involves stirring a solution homogeneously and allowing particles to be formed stably.

Reference Signs List 1 sample cuvet, 2 ... stirring means, 3 ... incident light source, 4 ... backscattered light detecting means (first scattered light detecting means), 5 ... scattered light fluctuation measuring means, 6 ... gel particle production determining means, 7 ... thermostatic chamber, 8 ... stray light removing means, 9 ... display means, 10 ... second scattered light detecting means, G ... gel particle, S ... sample, R ... reagent, W ... mixed solution, Bm ... light.

The invention claimed is:

1. A gel particle measurement device for measuring particles produced from a target substance in a sample through a gelation reaction, the gel particle measurement device comprising:
   sample cuvette comprising an incident portion through which light enters, and accommodating a sample containing a target substance to be measured and a solution containing a reagent that causes gelation of the target substance;
   a stirring device configured to stir a mixed solution comprising the sample and the solution containing the reagent in the sample cuvette so as to inhibit gelation of the entire mixed solution;
   an incident light source provided outside the incident portion of the sample cuvette, for irradiating the mixed solution comprising the sample and the solution containing the reagent in the sample cuvette with coherent light;
   a backscattered light detecting device provided outside the incident portion of the sample cuvette on the same side on which the incident light source is provided, and includes a light receiving part surrounding incident light which enters the sample cuvette front the incident light source, the backscattered light detecting device configured to detect a backscattered light component, which returns toward the incident light source, in a light scattered in the mixed solution comprising the sample and the solution containing the reagent in the sample cuvette;
   a scattered light fluctuation device configured to measure a fluctuation component of scattered light based on a detection output from the backscattered light detecting device;
   a stray light removing device provided on the opposite side on which the incident light source and the backscattered light detecting device are provided in the sample cuvette or around the sample cuvette, the stray light removing device configured to remove a stray light component, which is generated by transmission or scattering, except the backscattered light component, which returns toward the incident light source in the mixed solution, in irradiation light from the incident light source, and
   a gel particle production device configured to determine, based on a result of measurement by the scattered light fluctuation device, a production state of gel particles, which includes at least a starting point of production of the gel particles in the mixed solution, which leads to timing of phase transition of the mixed solution from a sol phase to a gel phase.

2. The gel particle measurement device according to claim 1, wherein the incident light source comprises a laser light source.

3. The gel particle measurement device according to claim 1, wherein the sample cuvette further comprises, in a cell container, a stirrer bar of the stirring device capable of directly stirring the sample and the solution containing the reagent.

4. The gel particle measurement device according to claim 1, wherein the sample cuvette is placed in a thermostatic chamber.

5. The gel particle measurement device according to claim 1, further comprising display device configured to display a result of determination by the gel particle production device.

6. The gel particle measurement device according to claim 1, wherein the backscattered light detecting device comprises a ring-shaped detection surface surrounding incident light which enters the sample cuvette from the incident light source.

7. The gel particle measurement device according to claim 1, wherein the backscattered light detecting device comprises a light-guiding member made of a light-transmissive fiber bundle surrounding incident light which enters the sample cuvette from the incident light source, the light-guiding member having one end functioning as a light introduction surface, the backscattered light detecting device having a detection surface placed corresponding to another end of the light-guiding member.

8. The gel particle measurement device according to claim 1, further comprising:
   a first scattered light detecting device configured to serve as the backscattered light detecting device to detect the backscattered light component, which returns toward the incident light source, in the light scattered in the mixed solution;
   a second scattered light detecting device configured to detect a scattered light component except the backscattered light component, which returns toward the incident light source, in the light scattered in the mixed solution; and
   a scattered light fluctuation device to measure a fluctuation component of each scattered light based on detection outputs from the first and the second scattered light detecting device,
   wherein the gel particle production device is configured to:
      determine the starting point of production of the gel particles in the mixed solution based on a result of measurement of the fluctuation component in the detection output from the first scattered light detecting device; and
      determine production state information of the gel particles at points except the starting point of production of the gel particles in the mixed solution based on a result of measurement of the fluctuation component in the detection output from the first scattered light detecting device and the detection output from the second scattered light detecting device or based on a result of measurement of the fluctuation component in the detection output from the second scattered light detecting device.

9. The gel particle measurement device according to claim 1, wherein the target substance as the measuring object comprises an endotoxin and the reagent for gelating the endotoxin comprises a reagent.

10. The gel particle measurement device according to claim 1, wherein the backscattered light detecting device further comprises a ring-shaped detection surface surrounding incident light which enters the sample cuvette from the incident light source.

11. The gel particle measurement device according to claim 1, wherein the backscattered light detecting device further comprises a light-guiding member made of a light-transmissive fiber bundle surrounding incident light which enters the sample cuvette from the incident light source, the light-guiding member having one end functioning as a light introduction surface, the backscattered light detecting device having a detection surface placed corresponding to another end of the light-guiding member.

* * * * *